(12) United States Patent
Kudo

(10) Patent No.: US 12,721,722 B2
(45) Date of Patent: Sep. 1, 2026

(54) INTRAOCULAR LENS INJECTOR AND ITS DESIGN METHOD

(71) Applicant: Hoya Medical Singapore Pte. Ltd., Singapore (SG)

(72) Inventor: Kazunori Kudo, Saku (JP)

(73) Assignee: Hoya Medical Singapore Pte. Ltd., Singapore (SG)

( * ) Notice: Subject to any disclaimer, the term of this patent is extended or adjusted under 35 U.S.C. 154(b) by 642 days.

(21) Appl. No.: 18/044,235

(22) PCT Filed: Aug. 30, 2021

(86) PCT No.: PCT/JP2021/031663

§ 371 (c)(1),
(2) Date: Mar. 7, 2023

(87) PCT Pub. No.: WO2022/054619

PCT Pub. Date: Mar. 17, 2022

(65) Prior Publication Data

US 2023/0372083 A1 Nov. 23, 2023

(30) Foreign Application Priority Data

Sep. 9, 2020 (JP) ................................ 2020-151086

(51) Int. Cl.
*A61F 2/16* (2006.01)

(52) U.S. Cl.
CPC ........ *A61F 2/167* (2013.01); *A61F 2240/001* (2013.01)

(58) Field of Classification Search
CPC ... A61F 2/167; A61F 2240/001; A61F 2/1678
See application file for complete search history.

(56) References Cited

U.S. PATENT DOCUMENTS 2,761,446 A 9/1956 Reed
3,212,685 A 10/1965 Swan
(Continued)

FOREIGN PATENT DOCUMENTS

CN 101073519 A 11/2007
CN 204601363 U 9/2015
(Continued)

OTHER PUBLICATIONS

PCT International Preliminary Examination Report dated Mar. 23, 2023 for PCT App. Ser. No. PCT/JP2021/031663.
(Continued)

*Primary Examiner* — Ashley L Fishback
*Assistant Examiner* — Chima U Igboko
(74) *Attorney, Agent, or Firm* — Henricks Slavin LLP

(57) ABSTRACT

There is provided an intraocular lens injector 1 that advances an intraocular lens 4 including an optical portion 41 with an optical function and support portions **42*a* and 42*b* that extend from the optical portion 41 through a tube while folding the lens, and emits the lens from a nozzle, wherein protrusions 15 are located at both the left and right corners at an upper side of an inner wall 30 of the tube, in a cross-sectional view perpendicular to an advancement direction of the intraocular lens 4, so that the protrusions 15 prevent the optical portion 41 and the support portions 42*a*, 42*b* from entering both the left and right corners, when the intraocular lens 4** is folded while advancing. Its related art is also provided.

13 Claims, 13 Drawing Sheets

(56) References Cited

U.S. PATENT DOCUMENTS 4,205,747 A 6/1980 Gilliam et al.
4,269,307 A 5/1981 LaHaye
4,423,809 A 1/1984 Mazzocco
4,573,998 A 3/1986 Mazzocco
4,608,049 A 8/1986 Kelman
4,634,423 A 1/1987 Bailey
4,681,102 A 7/1987 Bartell
4,697,697 A 10/1987 Graham et al.
4,699,140 A 10/1987 Holmes
4,702,244 A 10/1987 Mazzocco
4,715,373 A 12/1987 Mazzocco et al.
4,747,404 A 5/1988 Jampel et al.
4,750,498 A 6/1988 Graham
4,759,359 A 7/1988 Willis et al.
4,763,650 A 8/1988 Hauser
4,765,329 A 8/1988 Cumming et al.
4,769,034 A 9/1988 Poley
4,781,719 A 11/1988 Kelman
4,787,904 A 11/1988 Severin
4,810,249 A 3/1989 Haber et al.
4,819,631 A 4/1989 Poley
4,834,094 A 5/1989 Patton
4,836,201 A 6/1989 Patton
4,862,885 A 9/1989 Cumming
4,880,000 A 11/1989 Holmes et al.
4,919,130 A 4/1990 Stoy et al.
4,934,363 A 6/1990 Smith et al.
4,955,889 A 9/1990 Van Gent
4,976,716 A 12/1990 Cumming
4,988,352 A 1/1991 Poley
4,994,028 A 2/1991 Leonard et al.
5,066,297 A 11/1991 Cumming
5,098,439 A 3/1992 Hill et al.
5,123,905 A 6/1992 Kelman
5,139,501 A 8/1992 Klaas
5,171,241 A 12/1992 Buboltz et al.
5,176,686 A 1/1993 Poley
5,178,622 A 1/1993 Lehner, II
5,190,552 A 3/1993 Kelman
5,190,553 A 3/1993 Kanert et al.
5,222,972 A 6/1993 Hill et al.
5,242,450 A 9/1993 McDonald
5,259,395 A 11/1993 Li
5,275,604 A 1/1994 Rheinish et al.
5,281,227 A 1/1994 Sussman
5,304,182 A 4/1994 Rheinish et al.
5,354,333 A 10/1994 Kammann et al.
5,395,378 A 3/1995 McDonald
5,425,734 A 6/1995 Blake
5,454,818 A 10/1995 Hambleton et al.
5,468,246 A 11/1995 Blake
5,474,562 A 12/1995 Orchowski et al.
5,494,484 A 2/1996 Feingold
5,496,328 A 3/1996 Nakajima et al.
5,499,987 A 3/1996 Feingold
5,562,676 A 10/1996 Brady et al.
5,571,113 A 11/1996 McDonald
5,578,042 A 11/1996 Cumming
5,582,613 A 12/1996 Brady
5,582,614 A 12/1996 Feingold
5,584,304 A 12/1996 Brady
5,616,148 A 4/1997 Eagles et al.
5,620,450 A 4/1997 Eagles et al.
5,643,275 A 7/1997 Blake
5,643,276 A 7/1997 Zaleski
5,645,534 A 7/1997 Chanoch
5,653,715 A 8/1997 Reich et al.
5,653,753 A 8/1997 Brady et al.
5,702,402 A 12/1997 Brady
5,702,441 A 12/1997 Zhou
5,716,364 A 2/1998 Makker et al.
5,728,075 A 3/1998 Levander
5,728,102 A 3/1998 Feingold et al.
5,735,858 A 4/1998 Makker et al.
5,766,181 A 6/1998 Chambers et al.
5,772,666 A 6/1998 Feingold et al.
5,772,667 A 6/1998 Blake
5,776,138 A 7/1998 Vidal et al.
5,800,442 A 9/1998 Wolf et al.
5,803,925 A 9/1998 Yang et al.
5,807,400 A 9/1998 Chambers et al.
5,810,833 A 9/1998 Brady et al.
5,810,834 A 9/1998 Heyman
5,860,984 A 1/1999 Chambers et al.
5,860,986 A 1/1999 Reich et al.
5,868,751 A 2/1999 Feingold
5,868,752 A 2/1999 Makker et al.
5,873,879 A 2/1999 Figueroa et al.
5,876,406 A 3/1999 Wolf et al.
5,876,407 A 3/1999 Makker et al.
5,876,440 A 3/1999 Feingold
5,891,152 A 4/1999 Feingold
5,902,307 A 5/1999 Feingold et al.
5,919,197 A 7/1999 McDonald
5,921,989 A 7/1999 Deacon et al.
5,928,245 A 7/1999 Wolf et al.
5,941,886 A 8/1999 Feingold
5,942,277 A 8/1999 Makker et al.
5,944,725 A 8/1999 Cicenas
5,947,974 A 9/1999 Brady et al.
5,947,975 A 9/1999 Kikuchi et al.
5,957,748 A 9/1999 Ichiha
5,957,896 A 9/1999 Bendek et al.
6,001,107 A 12/1999 Feingold
6,010,510 A 1/2000 Brown et al.
6,022,358 A 2/2000 Wolf et al.
6,048,348 A 4/2000 Chambers et al.
6,050,999 A 4/2000 Paraschac et al.
6,051,000 A 4/2000 Heyman
6,056,757 A 5/2000 Feingold et al.
6,056,758 A 5/2000 Vidal et al.
6,059,791 A 5/2000 Chambers
6,074,397 A 6/2000 Chambers et al.
6,083,230 A 7/2000 Makker et al.
6,093,193 A 7/2000 Makker et al.
6,129,733 A 10/2000 Brady et al.
6,142,999 A 11/2000 Brady et al.
6,143,000 A 11/2000 Feingold
6,162,229 A 12/2000 Feingold et al.
6,174,315 B1 1/2001 Chambers et al.
6,214,015 B1 4/2001 Reich et al.
6,241,737 B1 6/2001 Feingold
6,248,111 B1 6/2001 Glick et al.
6,251,114 B1 6/2001 Farmer et al.
6,254,607 B1 7/2001 Makker et al.
6,267,768 B1 7/2001 Deacon
6,283,975 B1 9/2001 Glick et al.
6,283,976 B1 9/2001 Portney
6,312,433 B1 11/2001 Butts
6,334,862 B1 1/2002 Vidal et al.
6,336,932 B1 1/2002 Figueroa et al.
6,355,046 B2 3/2002 Kikuchi et al.
6,371,960 B2 4/2002 Heyman et al.
6,386,357 B1 5/2002 Egawa
6,387,101 B1 5/2002 Butts et al.
6,398,788 B1 6/2002 Makker et al.
6,406,481 B2 6/2002 Feingold et al.
6,428,545 B2 8/2002 Portney
6,447,519 B1 9/2002 Brady et al.
6,447,520 B1 9/2002 Ott et al.
6,468,282 B2 10/2002 Kikuchi et al.
6,471,708 B2 10/2002 Green
6,491,697 B1 12/2002 Clark et al.
6,497,708 B1 12/2002 Cumming
6,500,181 B1 12/2002 Portney
6,503,275 B1 1/2003 Cumming
6,506,195 B2 1/2003 Chambers et al.
6,537,283 B2 3/2003 Van Noy
6,540,754 B2 4/2003 Brady
6,554,839 B2 4/2003 Brady
6,558,395 B2 5/2003 Hjertman et al.
6,605,093 B1 8/2003 Blake
6,607,537 B1 8/2003 Binder
6,629,979 B1 10/2003 Feingold

(56) References Cited

U.S. PATENT DOCUMENTS 6,666,871 B2 12/2003 Kikuchi et al.
6,679,891 B2 1/2004 Makker et al.
6,685,740 B2 2/2004 Figueroa et al.
6,712,848 B1 3/2004 Wolf et al.
6,723,104 B2 4/2004 Ott
6,733,507 B2 5/2004 McNicholas et al.
6,749,631 B1 6/2004 Pietrini et al.
6,793,674 B2 9/2004 Zapata
6,858,033 B2 2/2005 Kobayashi
6,921,405 B2 7/2005 Feingold et al.
6,923,815 B2 8/2005 Brady et al.
6,976,989 B1 12/2005 Vincent
7,014,641 B2 3/2006 Kobayashi et al.
7,025,782 B2 4/2006 Kobayashi et al.
7,033,366 B2 4/2006 Brady
7,037,312 B2 5/2006 Kikuchi et al.
7,074,227 B2 7/2006 Portney
7,097,649 B2 8/2006 Meyer
7,131,976 B2 11/2006 Kobayashi et al.
7,156,854 B2 1/2007 Brown et al.
7,348,038 B2 3/2008 Makker et al.
7,422,604 B2 9/2008 Vaquero et al.
7,429,263 B2 9/2008 Vaquero et al.
7,458,976 B2 12/2008 Peterson et al.
7,476,230 B2 1/2009 Ohno et al.
7,494,505 B2 2/2009 Kappelhof et al.
7,645,300 B2 1/2010 Tsai
8,273,122 B2 9/2012 Anderson
8,382,769 B2 2/2013 Inoue
8,460,311 B2 6/2013 Ishii
8,470,032 B2 6/2013 Inoue et al.
8,475,526 B2 7/2013 Pynson
8,475,528 B2 7/2013 Ichinohe et al.
8,523,877 B2 9/2013 Ichinohe et al.
8,523,941 B2 9/2013 Ichinohe et al.
8,535,375 B2 9/2013 Ichinohe et al.
8,545,512 B2 10/2013 Ichinohe et al.
8,574,239 B2 11/2013 Ichinohe et al.
8,603,103 B2 12/2013 Kudo et al.
8,647,382 B2 2/2014 Kudo et al.
8,702,795 B2 4/2014 Shoji et al.
8,747,465 B2 6/2014 Someya et al.
8,968,328 B2 3/2015 Ichinohe et al.
9,114,006 B2 8/2015 Inoue
9,114,007 B2 8/2015 Ichinohe et al.
9,186,246 B2 11/2015 Inoue
9,220,593 B2 12/2015 Ichinohe
9,237,947 B2 1/2016 Valle
9,289,288 B2 3/2016 Someya et al.
9,314,373 B2 4/2016 Kudo et al.
9,326,847 B2 5/2016 Sanger
9,364,320 B2 6/2016 Ichinohe et al.
9,554,894 B2 1/2017 Inoue
9,572,710 B1 2/2017 Kudo et al.
9,655,718 B2 5/2017 Kudo
9,687,340 B2 6/2017 Anderson
9,877,826 B2 1/2018 Kudo et al.
9,901,442 B2 2/2018 Kudo et al.
9,907,647 B2 3/2018 Inoue
9,980,811 B2 5/2018 Kudo et al.
10,039,668 B2 8/2018 Kudo et al.
10,231,826 B2 3/2019 Hangya et al.
10,383,723 B2 8/2019 Kudo
10,390,940 B2 8/2019 Someya et al.
10,405,971 B2 9/2019 Someya et al.
10,517,717 B2 12/2019 Inoue
10,799,339 B2 10/2020 Kudo et al.
10,849,738 B2 12/2020 Kudo et al.
11,033,382 B2 6/2021 Watanabe et al.
11,439,499 B2 9/2022 Wensrich et al.
11,938,019 B2 3/2024 Someya et al.
12,076,231 B2 9/2024 Noda et al.
12,257,145 B2 3/2025 Kudo
12,414,852 B2 9/2025 Watanabe et al.
12,478,467 B2 11/2025 Kudo
2001/0007942 A1 7/2001 Kikuchi et al.
2001/0020171 A1 9/2001 Heyman
2002/0082609 A1 6/2002 Green
2002/0103490 A1 8/2002 Brady
2002/0151904 A1 10/2002 Feingold et al.
2002/0165610 A1 11/2002 Waldock
2002/0193805 A1 12/2002 Ott et al.
2003/0036765 A1 2/2003 Van Noy
2003/0040755 A1 2/2003 Meyer
2003/0050647 A1 3/2003 Brady
2003/0088253 A1 5/2003 Seil
2003/0139749 A1 7/2003 Kikuchi et al.
2003/0181921 A1 9/2003 Jeannin
2003/0195522 A1 10/2003 McNicholas
2003/0212406 A1 11/2003 Kobayashi et al.
2003/0212407 A1 11/2003 Kikuchi
2003/0212408 A1 11/2003 Kobayashi
2003/0212409 A1 11/2003 Kobayashi et al.
2004/0039345 A1 2/2004 Benz et al.
2004/0111094 A1 6/2004 Meyer
2004/0116937 A1 6/2004 Portney
2004/0117012 A1 6/2004 Vincent
2004/0127911 A1 7/2004 Figueroa
2004/0147938 A1 7/2004 Dusek et al.
2004/0186428 A1 9/2004 Ray
2004/0238392 A1 12/2004 Peterson et al.
2004/0243141 A1 12/2004 Brown et al.
2005/0033308 A1 2/2005 Callahan et al.
2005/0049605 A1 3/2005 Vaquero et al.
2005/0049606 A1 3/2005 Vaquero et al.
2005/0055011 A1 3/2005 Enggaard
2005/0125000 A1 6/2005 Tourrette et al.
2005/0143750 A1 6/2005 Vaquero
2005/0182419 A1 8/2005 Tsai
2005/0222578 A1 10/2005 Vaquero
2005/0261703 A1 11/2005 Feingold et al.
2006/0085013 A1 4/2006 Dusek
2006/0142781 A1 6/2006 Pynson et al.
2006/0167466 A1 7/2006 Dusek
2006/0173540 A1 8/2006 Vincent
2006/0200167 A1 9/2006 Peterson et al.
2006/0229633 A1 10/2006 Shepherd
2006/0235429 A1 10/2006 Lee et al.
2006/0293694 A1 12/2006 Futamura
2007/0000801 A1 1/2007 Mauran et al.
2007/0005135 A1 1/2007 Makker et al.
2007/0168026 A1 7/2007 Nagasaka
2007/0173860 A1 7/2007 Iwasaki
2007/0270945 A1 11/2007 Kobayashi
2008/0027460 A1 1/2008 Kobayashi
2008/0033449 A1 2/2008 Cole et al.
2008/0058830 A1 3/2008 Cole et al.
2008/0086146 A1 4/2008 Ishii et al.
2008/0097459 A1 4/2008 Kammerlander et al.
2008/0221584 A1 9/2008 Downer
2009/0036898 A1 2/2009 Ichinohe
2009/0043313 A1 2/2009 Ichinohe
2009/0112223 A1 4/2009 Downer et al.
2009/0125034 A1 5/2009 Pynson
2009/0138022 A1 5/2009 Tu et al.
2009/0204122 A1 8/2009 Ichinohe et al.
2009/0216244 A1 8/2009 Pynson
2009/0248031 A1 10/2009 Ichinohe
2009/0270876 A1 10/2009 Hoffmann et al.
2009/0292293 A1 11/2009 Bogaert et al.
2010/0082037 A1 4/2010 Kobayashi et al.
2010/0094309 A1 4/2010 Boukhny et al.
2010/0106160 A1 4/2010 Tsai
2010/0161049 A1 6/2010 Inoue
2010/0185206 A1 7/2010 Ichinohe et al.
2010/0217273 A1 8/2010 Someya et al.
2010/0286704 A1 11/2010 Ichinohe et al.
2010/0331808 A1 12/2010 Py et al.
2011/0046633 A1 2/2011 Pankin et al.
2011/0046635 A1 2/2011 Pankin et al.
2011/0082463 A1 4/2011 Inoue
2011/0098717 A1 4/2011 Inoue
2011/0144654 A1 6/2011 Isaacs et al.
2011/0172676 A1 7/2011 Chen

(56) References Cited

U.S. PATENT DOCUMENTS

| | | | | |
|---|---|---|---|---|
| 2011/0264101 | A1 | 10/2011 | Inoue et al. | |
| 2011/0270264 | A1 | 11/2011 | Shoji et al. | |
| 2011/0288557 | A1 | 11/2011 | Kudo et al. | |
| 2012/0022548 | A1 | 1/2012 | Zacharias | |
| 2012/0022549 | A1 | 1/2012 | Someya et al. | |
| 2012/0071887 | A1 | 3/2012 | Ichinohe et al. | |
| 2012/0123438 | A1 | 5/2012 | Horvath et al. | |
| 2012/0221102 | A1* | 8/2012 | Tanaka | A61F 2/167 623/6.12 |
| 2013/0006259 | A1 | 1/2013 | Sanger | |
| 2013/0018460 | A1 | 1/2013 | Anderson | |
| 2013/0085507 | A1 | 4/2013 | Nagasaka | |
| 2013/0226193 | A1* | 8/2013 | Kudo | A61F 9/0008 606/107 |
| 2013/0245635 | A1 | 9/2013 | Inoue | |
| 2013/0345713 | A1 | 12/2013 | Cole et al. | |
| 2014/0081284 | A1 | 3/2014 | Ichinohe et al. | |
| 2014/0107660 | A1 | 4/2014 | Ichinohe et al. | |
| 2014/0114323 | A1 | 4/2014 | Kudo et al. | |
| 2014/0135784 | A1 | 5/2014 | Maroscheck et al. | |
| 2014/0180299 | A1 | 6/2014 | Ichinohe et al. | |
| 2014/0180300 | A1 | 6/2014 | Ichinohe et al. | |
| 2014/0194890 | A1 | 7/2014 | Kudo et al. | |
| 2014/0200588 | A1 | 7/2014 | Anderson et al. | |
| 2014/0222013 | A1* | 8/2014 | Argal | A61F 2/1678 606/107 |
| 2014/0276901 | A1 | 9/2014 | Auld | |
| 2014/0296863 | A1 | 10/2014 | Anderson et al. | |
| 2015/0045805 | A1 | 2/2015 | Kontur et al. | |
| 2015/0157500 | A1 | 6/2015 | Midorikawa | |
| 2015/0327992 | A1 | 11/2015 | Wagner et al. | |
| 2016/0000556 | A1 | 1/2016 | Perera | |
| 2016/0058554 | A1 | 3/2016 | Anderson et al. | |
| 2016/0113759 | A1 | 4/2016 | Inoue | |
| 2016/0151150 | A1 | 6/2016 | Sato | |
| 2016/0193038 | A1 | 7/2016 | Kudo et al. | |
| 2016/0256316 | A1 | 9/2016 | Van Noy et al. | |
| 2016/0270907 | A1 | 9/2016 | Attinger | |
| 2016/0331587 | A1 | 11/2016 | Yamada et al. | |
| 2016/0346077 | A1 | 12/2016 | Someya et al. | |
| 2017/0079772 | A1 | 3/2017 | Kudo | |
| 2017/0119522 | A1 | 5/2017 | Auld et al. | |
| 2017/0151056 | A1 | 6/2017 | Inoue | |
| 2017/0202662 | A1 | 7/2017 | Someya et al. | |
| 2017/0252149 | A1 | 9/2017 | Kudo et al. | |
| 2017/0252150 | A1 | 9/2017 | Kudo et al. | |
| 2017/0258582 | A1 | 9/2017 | Kudo et al. | |
| 2017/0354493 | A1 | 12/2017 | Andersen et al. | |
| 2018/0014996 | A1 | 1/2018 | Asbaghi | |
| 2018/0200046 | A1 | 7/2018 | Brown et al. | |
| 2018/0200047 | A1* | 7/2018 | Wu | A61F 2/1678 |
| 2018/0228650 | A1 | 8/2018 | Putallaz et al. | |
| 2018/0250125 | A1 | 9/2018 | Kudo et al. | |
| 2018/0353287 | A1 | 12/2018 | Kudo et al. | |
| 2019/0151078 | A1 | 5/2019 | Watanabe et al. | |
| 2019/0192284 | A1 | 6/2019 | Watanabe et al. | |
| 2020/0015959 | A1 | 1/2020 | Wensrich et al. | |
| 2020/0113674 | A1 | 4/2020 | Someya et al. | |
| 2021/0145570 | A1 | 5/2021 | Kudo | |
| 2021/0161653 | A1 | 6/2021 | Noda et al. | |
| 2021/0205071 | A1 | 7/2021 | Chini | |
| 2022/0151767 | A1 | 5/2022 | Kudo | |
| 2023/0033115 | A1 | 2/2023 | Watanabe et al. | |
| 2023/0225858 | A1 | 7/2023 | Someya et al. | |
| 2023/0301833 | A1 | 9/2023 | Wu | |
| 2023/0338138 | A1 | 10/2023 | Kelp et al. | |
| 2024/0268951 | A1 | 8/2024 | Maroscheck et al. | |
| 2024/0374376 | A1 | 11/2024 | Noda et al. | |
| 2024/0415634 | A1 | 12/2024 | Kudo | |

FOREIGN PATENT DOCUMENTS

| | | | |
|---|---|---|---|
| DE | 3610925 | | 10/1987 |
| DE | 4110278 | | 10/1992 |
| DE | 19544119 | A1 | 5/1997 |
| DE | 20219445 | U1 | 3/2003 |
| EP | 0363213 | | 4/1990 |
| EP | 0727966 | | 9/2003 |
| EP | 1360947 | A1 | 11/2003 |
| EP | 1502559 | A1 | 2/2005 |
| EP | 1790317 | A2 | 5/2007 |
| EP | 1808150 | A1 | 7/2007 |
| EP | 1832247 | A1 | 9/2007 |
| EP | 1338254 | B1 | 12/2008 |
| EP | 2074961 | A1 | 7/2009 |
| EP | 2255751 | A1 | 12/2010 |
| EP | 2286763 | A1 | 2/2011 |
| EP | 2286764 | A1 | 2/2011 |
| EP | 2368526 | A1 | 9/2011 |
| EP | 2574308 | A2 | 4/2013 |
| EP | 2853236 | A2 | 4/2015 |
| EP | 3391855 | A1 | 10/2018 |
| FR | 2749752 | A | 12/1997 |
| JP | 63-197453 | A | 8/1988 |
| JP | 4-212350 | A | 8/1992 |
| JP | 5-103803 | A | 4/1993 |
| JP | 5-103808 | | 4/1993 |
| JP | 5-103809 | | 4/1993 |
| JP | 8-019558 | A | 1/1996 |
| JP | 8-024282 | A | 1/1996 |
| JP | 8-505540 | | 6/1996 |
| JP | 9-506285 | A | 6/1997 |
| JP | 11-113939 | A | 4/1999 |
| JP | 11-506357 | A | 6/1999 |
| JP | 2000-516487 | A | 12/2000 |
| JP | 2000-516488 | A | 12/2000 |
| JP | 2001-502563 | | 2/2001 |
| JP | 2001-104347 | A | 4/2001 |
| JP | 2001-259033 | | 9/2001 |
| JP | 2002-516709 | A | 6/2002 |
| JP | 2002-355268 | A | 12/2002 |
| JP | 2002-541912 | A | 12/2002 |
| JP | 2003-144480 | A | 5/2003 |
| JP | 3412106 | B2 | 6/2003 |
| JP | 2003-210498 | A | 7/2003 |
| JP | 2003-527162 | A | 9/2003 |
| JP | 2003-325569 | A | 11/2003 |
| JP | 2003-325570 | A | 11/2003 |
| JP | 2003-325572 | A | 11/2003 |
| JP | 2004-024854 | A | 1/2004 |
| JP | 2004-041271 | A | 2/2004 |
| JP | 2004-188194 | A | 7/2004 |
| JP | 2004-344213 | A | 12/2004 |
| JP | 2004-351196 | A | 12/2004 |
| JP | 2006-014963 | A | 1/2006 |
| JP | 2006-181269 | A | 7/2006 |
| JP | 2006-297146 | A | 11/2006 |
| JP | 2006-333924 | A | 12/2006 |
| JP | 2006-333980 | A | 12/2006 |
| JP | 2006-333981 | A | 12/2006 |
| JP | 2007-503872 | A | 3/2007 |
| JP | 2007-152010 | A | 6/2007 |
| JP | 2007-181604 | A | 7/2007 |
| JP | 2007-222309 | A | 9/2007 |
| JP | 2007-244570 | A | 9/2007 |
| JP | 2007-526091 | A | 9/2007 |
| JP | 2007-307168 | A1 | 11/2007 |
| JP | 2008-012016 | A | 1/2008 |
| JP | 2008-521535 | A | 6/2008 |
| JP | 2008-212689 | A | 9/2008 |
| JP | 2008-237274 | A | 10/2008 |
| JP | 2009-028223 | A | 2/2009 |
| JP | 2009-072221 | A | 4/2009 |
| JP | 2011-019987 | A | 2/2011 |
| JP | 2011-087976 | A | 5/2011 |
| JP | 2011-160858 | A | 8/2011 |
| JP | 2011-160859 | A | 8/2011 |
| JP | 2013-144163 | A | 7/2013 |
| JP | 2014-050484 | A | 3/2014 |
| JP | 2014-079630 | A | 5/2014 |
| JP | 2016049321 | A | 4/2016 |
| JP | 2016-137122 | A | 8/2016 |
| JP | 2022-039196 | A | 3/2022 |

(56) References Cited

FOREIGN PATENT DOCUMENTS

| | | | |
|---|---|---|---|
| JP | 2025-079474 | A | 5/2025 |
| WO | WO9407436 | A1 | 4/1994 |
| WO | WO9513022 | A1 | 5/1995 |
| WO | WO9628122 | A1 | 9/1996 |
| WO | WO9715253 | A1 | 5/1997 |
| WO | WO9812969 | A1 | 4/1998 |
| WO | WO9937247 | A1 | 7/1999 |
| WO | WO9958086 | A1 | 11/1999 |
| WO | WO9959668 | A1 | 11/1999 |
| WO | WO0045746 | A1 | 8/2000 |
| WO | WO0062712 | A1 | 10/2000 |
| WO | WO2002071982 | A1 | 9/2002 |
| WO | WO2002096322 | A1 | 12/2002 |
| WO | WO2004041323 | A2 | 5/2004 |
| WO | WO2004105649 | A1 | 12/2004 |
| WO | WO2005023154 | A1 | 3/2005 |
| WO | WO2005030097 | A1 | 4/2005 |
| WO | WO2005070341 | A1 | 8/2005 |
| WO | WO2005084588 | A1 | 9/2005 |
| WO | WO2006070628 | A1 | 7/2006 |
| WO | WO2006080191 | A1 | 8/2006 |
| WO | WO2006090531 | A1 | 8/2006 |
| WO | WO2007037223 | A1 | 4/2007 |
| WO | WO2007080869 | A1 | 7/2007 |
| WO | WO2007097221 | A1 | 8/2007 |
| WO | WO2008149794 | A1 | 12/2008 |
| WO | WO2008149795 | A1 | 12/2008 |
| WO | WO2009058929 | A1 | 7/2009 |
| WO | WO2009148091 | A1 | 12/2009 |
| WO | WO2010028873 | A1 | 3/2010 |
| WO | WO2010064670 | A1 | 6/2010 |
| WO | WO2011126144 | A1 | 10/2011 |
| WO | WO2011155636 | A1 | 12/2011 |
| WO | WO2012086797 | A1 | 6/2012 |
| WO | WO2012155887 | A1 | 11/2012 |
| WO | WO2015012312 | A1 | 1/2015 |
| WO | WO2016191764 | A1 | 12/2016 |
| WO | WO2018151141 | A1 | 8/2018 |
| WO | WO2019130028 | A1 | 7/2019 |

OTHER PUBLICATIONS

Presentation given by James P. McCulley, titled "Benefits of Newest Generation Fully Preloaded Aspheric IOL Delivery System," on Sep. 16, 2008 at the "Aspheric IOLs" free paper session of the 2008 Congress of the European Society of Cataract and Refractive Surgery, in Berlin, Germany.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, U.S. Pat. No. 11,617,643.
U.S. Appl. No. 18/186,167, filed Mar. 18, 2023, US 20230225858A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375 .
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, U.S. Pat. No. 11,033,382.
U.S. Appl. No. 17/055,253, filed Nov. 13, 2020, US 20210161653A1.
U.S. Appl. No. 17/055,186, filed Nov. 13, 2020, US 20210145570A1.
U.S. Appl. No. 17/435,762, filed Sep. 2, 2021, US 20220151767A1.
U.S. Appl. No. 17/801,364, filed Aug. 22, 2022, US 20230033115A1.
U.S. Appl. No. 18/186,167, filed Mar. 18, 2023, U.S. Pat. No. 11,938,019.
U.S. Appl. No. 17/055,253, Nov. 13, 2020, U.S. Pat. No. 12,076,231.
U.S. Appl. No. 18/778,973, filed Jul. 20, 2024.
U.S. Appl. No. 17/055,186, Nov. 13, 2020, US 20210145570A1.
U.S. Appl. No. 18/694,985, filed Mar. 24, 2023.
EPO Extended European Search Report dated Sep. 17, 2024 for EPO App. Ser. No. 21866578.4.

* cited by examiner

INTRAOCULAR LENS INJECTOR AND ITS DESIGN METHOD

TECHNICAL FIELD

The present disclosure relates to an intraocular lens injector and its design method.

BACKGROUND ART

Cataract surgery involves the removal of a cloudy crystalline lens by ultrasonic emulsification followed by implantation of an intraocular lens into an eye. Currently, a soft intraocular lens made of a soft material such as silicone elastomer is injected into an eye using an intraocular lens injector.

When a soft intraocular lens is injected into an eye, the intraocular lens can be folded to reduce the size of the corneal incision.

An example of a known method of folding an intraocular lens is to fold it within an intraocular lens injector.

In Patent Documents 1 and 2, a plurality of protrusions are located on a top plate portion located in a passage through which the intraocular lens passes within the intraocular lens injector.

In Patent Document 1, the optical portion of an intraocular lens is oriented within the body so that it is pressed against the bottom side of the passage, thereby reducing the risk that a support portion gets caught between the wall of the through-hole and the optical surface opposite to the surface on which the support portion is folded (paragraph 0005, paragraph 0023, claim 1, FIG. 4, etc. of the Patent Document 1).

In Patent Document 2, a base part of the front support portion, which tends to lift up to a ceiling side when the optical portion is bent, can be pressed to a bottom side by a protruding portion (paragraphs 0051 to 0053, FIG. 5, etc. of Patent Document 2).

PRIOR ART DOCUMENT

Patent Document

Patent document 1: Japanese Patent Laid Open Publication No. 2016-49321

Patent document 2: Japanese Patent Laid Open Publication No. 2016-189925

SUMMARY OF DISCLOSURE

Problems to be Solved by Disclosure

The present inventor has studied and found that when advancing the intraocular lens through a tube while folding the lens, and emitting the lens from a nozzle, the presence of both left and right corners at an upper side of an inner wall of the tube affects the success or failure of folding of the intraocular lens.

FIG. 1 is a schematic cross-sectional diagram illustrating an inner wall of a tube leading to a nozzle of an intraocular lens injector.

The reference numeral 10 designates the inner wall of the tube. The reference numeral 41 indicates an optical portion of an intraocular lens.

FIG. 1(*a*) is a diagram illustrating how the optical portion is normally folded into a valley-fold shape, and FIG. 1(*b*) to FIG. 1(*d*) are diagrams illustrating how the optical portion can enter both left and right corners of the tube, forcing the lens to fold in an abnormal state.

FIG. 1(*b*) is a diagram illustrating how a gap G is formed between the optical portion and a lower-side inner wall of the tube. FIG. 1(*c*) is a diagram illustrating how the optical portion is folded into a mountain-fold shape. FIG. 1(*d*) is a diagram illustrating how the optical portion is folded in a state of a non-uniform mixture of valley-fold shape and mountain-fold shape.

With the configuration of FIG. 4 of Patent Document 1 or FIG. 5 of Patent Document 2, the optical portion can be in a state illustrated in FIG. 1(*b*) or FIG. 1(*d*). Especially in the state illustrated in FIG. 1(*b*), the support portion of the intraocular lens may enter the gap G formed by the optical portion.

It is a technical subject of the present disclosure to provide a technique for folding an intraocular lens with high accuracy.

Solution to Problem

FIG. 2 is a schematic cross-sectional diagram illustrating how protrusions are located at both left and right corners of the inner wall of the tube leading to the nozzle of the intraocular lens injector. The reference numeral 15 designates the protrusion. Hereinafter, indication of the reference numerals of the tube and the protrusion will be omitted.

The present inventor has intensively studied the above-described subject. As a result, it is found that the optical portion can be folded into the valley-fold shape while its posture being corrected to the state illustrated in FIG. 1(*a*) by adopting a shape of the inner wall (i.e., protrusion) such that neither the optical portion nor the support portion can enter both left and right corners at the upper side of the inner wall of the tube as illustrated in FIG. 2.

The configurations obtained based on the above findings are as follows.

A first aspect of the present disclosure provides an intraocular lens injector that advances an intraocular lens including an optical portion with an optical function and support portions that extend from the optical portion through a tube while folding the lens, and emits the lens from a nozzle, wherein protrusions are located at both left and right corners at an upper side of an inner wall of the tube, in a cross-sectional view perpendicular to an advancement direction of the intraocular lens, so that the protrusions prevent the optical portion and the support portions from entering both the left and right corners, when the intraocular lens is folded while advancing.

In a second aspect of the present disclosure that is an aspect of the first aspect, due to the protrusions, a space is formed between both the left and right corners, having a width in which the folded support portions can be accommodated.

In a third aspect of the present disclosure that is an aspect of the first or second aspect, the protrusions protrude inward horizontally and also protrude downward.

In a fourth aspect of the present disclosure that is an aspect of any one of the first to third aspects, the protrusions exist on the inner wall within any of a range of 0 to 20 degrees of an inclination angle from a horizontal line passing through a midpoint of up, down, left and right of a cross-sectional shape of the inner wall of the tube.

In a fifth aspect of the present disclosure that is an aspect of the fourth aspect, a minimum value of the inclination angle in the part where the protrusions exist is in a range of 0 to 15 degrees.

In a sixth aspect of the present disclosure that is an aspect of the fourth or fifth aspect, the protrusions have a shape that changes a concave shape of both left and right corners to a convex shape in the cross-sectional shape of the inner wall.

A seventh aspect of the present disclosure that is an aspect of any one of the first to sixth aspects, including:

a tucking pin that bends a front support portion in contact with the front support portion, the front support portion being one of the support portions and arranged in front, wherein the tucking pin stands uprightand when in contact with the front support portion becomes is a slope that is inclined towards the front.

An eighth aspect of the present disclosure that is an aspect of any one of the first to seventh aspects, which is a preload type with the intraocular lens previously loaded therein.

A ninth aspect of the present disclosure provides a design method of an intraocular lens injector that advances an intraocular lens including an optical portion with an optical function and a support portion that extends from the optical portion through a tube while folding the lens, and emits the lens from a nozzle, including:

providing protrusions at both left and right corners at an upper side of an inner wall of the tube, in a cross-sectional view perpendicular to an advancement direction of the intraocular lens, so that the protrusions prevent the optical portion and the support portions from entering both the left and right corners, when the intraocular lens is folded while advancing.

Other aspects of the present disclosure that can be combined with the above aspects are as follows.

Aspects according to the design method of the intraocular lens injector may have the characteristics of each of the above aspects.

The protrusion may be located at a position where the cross-sectional shape of the inner wall has the largest rate of change in curvature.

It is preferred that the protrusions exist on the inner wall suitably within a range of 0 to 15 degrees, and even more suitably within a range of 10 to 15 degrees of the above-described inclination angle θ.

For example, a width w in the Y1-Y2 direction of the protrusion (e.g., protrusion with stepped shape) located at the left corner is preferably 10 to 60% of a width W from a predetermined position of the vertical line formed by the midpoints of left and right (e.g., a midpoint O of up, down, left and right) to the left-hand inner wall. As for an actual size, the width in the Y1-Y2 direction of the protrusion located at the left corner is set to 0.5 to 2.5 mm. The same preferred examples may also be applied to the protrusion located at the right corner.

For example, as in FIG. 8C, a height h in the Z1-Z2 direction of the protrusion (e.g., protrusion with stepped shape) located at the left corner is preferably 30 to 80% of a height H between an upper-side inner wall and a lower-side inner wall on a vertical line passing through the above-described midpoint O of up, down, left and right. As for an actual size, the height in the Z1-Z2 direction of the protrusion located at the left corner is set to 0.5 to 1.5 mm. The same preferred examples may also be applied to the protrusion located at the right corner.

It is preferable to provide a protrusion at a position where the optical portion exists after the start of the folding of the intraocular lens. When the intraocular lens is installed in the lens installation portion, it is preferable to have a protrusion at least between the front end of the optical portion and the front end of the front support portion, the protrusion being preferably formed lengthwise in a front-back direction so as to include both the front ends.

Protrusions may be located on a lid of an injection cylinder main body, so that when the lid is closed, protrusions may be consequently formed at both the left and right corners in the tube.

A lower end of the protrusion may be displaced downward as it moves forward. In particular, when the intraocular lens is installed in the lens installation portion, it is preferable to displace the lower end of the protrusion downward as it moves forward, at least at the connection with a rear support portion for the optical portion.

The length of the protrusion in the X1-X2 direction is not limited as long as it is long enough to allow the tucking of the front support portion of the optical portion to be completed correctly when advancing the intraocular lens. As for an actual size, the length in the X1-X2 direction of the protrusion located at the left corner is set to 5 to 15 mm. The same preferred examples may also be applied to the protrusion located at the right corner.

Advantageous Effects of Disclosure

According to the present disclosure, a technique for folding an intraocular lens with high accuracy can be located.

DETAILED DESCRIPTION OF DISCLOSURE

Embodiments of the present disclosure will be described in detail hereafter, with reference to the drawings. Note that "to" represents being greater than or equal to a predetermined value and less than or equal to another predetermined value.

Further, in this embodiment, in describing a relative positional relationship and a direction of movement and the like of each part of the intraocular lens injector, one of the X axis directions is defined as X1 direction and the other direction is defined as X2 direction, and one of the Y axis directions is defined as Y1 direction and the other direction is defined as Y2 direction, and one of the Z axis directions is defined as Z1 direction and the other direction is defined as Z2 direction. Further, X1 direction is defined as a tip end side (frontward, advancement direction of the lens), X2 direction is defined as a rear end side (rearward), Y1 direction is defined as a right side (rightward), and Y2 direction is defined as a left side (leftward), Z1 direction is defined as an upper side (upward, thickness direction and a light axis direction when the intraocular lens is arranged), and Z2 direction is defined as a downside (downward). Among them, the X1 direction and X2 direction correspond to a length direction of the intraocular lens injector 1, and the Y1 direction and Y2 direction correspond to a width direction of the intraocular lens injector, and the Z1 direction and Z2 direction correspond to a height direction of the intraocular lens injector 1.

This embodiment illustrates a preload type intraocular lens injector with the intraocular lens previously loaded therein, but the present disclosure is not limited thereto.

Figure 3:
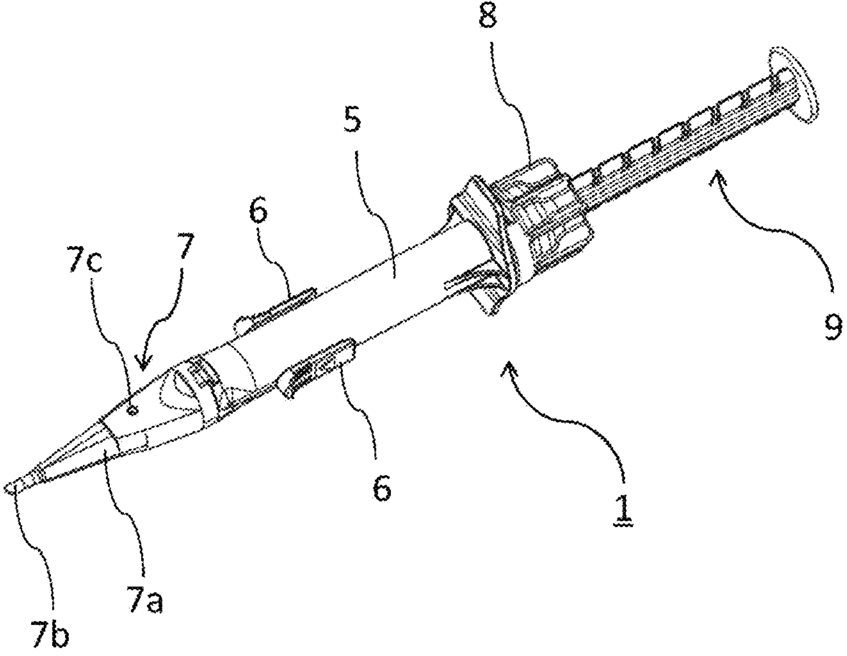
FIG. 3 is a perspective diagram illustrating a configuration example of an appearance of the intraocular lens injector.
Figure 3:
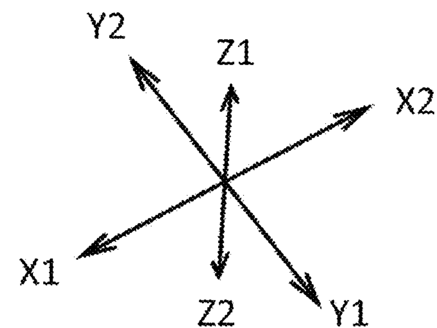

Basic Configuration of Intraocular Lens Injector According to this Embodiment FIG. 3 is a perspective diagram illustrating a configuration example of an appearance of the intraocular lens injector according to an embodiment of the present disclosure.

Figure 4:
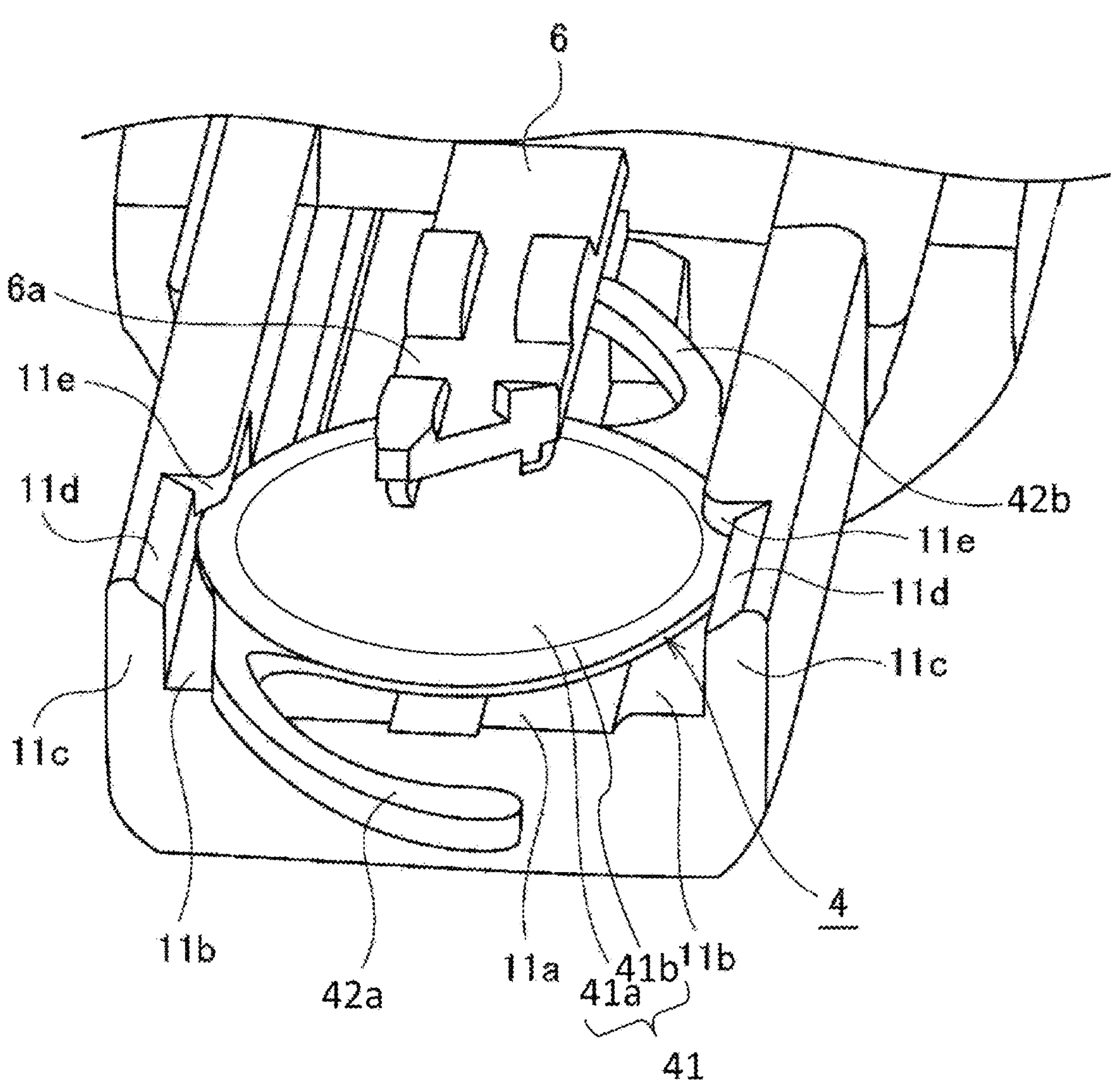
FIG. 4 is a perspective diagram illustrating a structure and an arrangement of a tip portion of the injector main body.

FIG. 4 is a perspective diagram illustrating a structure and an arrangement of a tip portion of the injector main body according to an embodiment of the present disclosure.

The intraocular lens injector 1 is used for injecting an intraocular lens into an eye. In this embodiment, as an example of the intraocular lens, there is located an one-piece type intraocular lens 4 (see FIG. 4) made of a soft material such as silicone elastomer or soft acrylic, which has an optical portion 41 including a circular effective optical portion 41*a* which performs an optical function and its peripheral portion 41*b*, as well as two support portions 42*a*, 42*b* that extend, curving outward from two positions on the outer circumferential portion of the optical portion 41. The reference numeral 42*a* indicates a front support portion arranged frontward when installed in the lens installation portion 11, and the reference numeral 42*b* indicates a rear support portion arranged rearward.

A case will be illustrated where the optical portion 41 of the intraocular lens 4 and base end sides of the support portions 42*a*, 42*b* connected to the optical portion 41 are configured by a soft material. This configuration facilitates folding of the intraocular lens 4. Note that end sides of the support portions 42*a*, 42*b* may similarly be configured by the soft material, or may be configured by a hard material (e.g., polyethylene, PMMA).

An effective optical portion 41*a* in the optical portion 41 has a shape that performs the optical function, a peripheral portion 41*b* is formed in an annular shape around the effective optical portion 41*a*, and the annular shape is like a flat plate. Of course, other configurations may be adopted. For example, the optical portion 41 may be configured only by the effective optical portion 41*a*. The peripheral portion 41*b* may be formed continuously with the effective optical portion 41*a*, that is, the peripheral portion 41*b* and the effective optical portion 41*a* may be smoothly connected to each other, forming a continuous surface.

The intraocular lens injector 1 has a configuration including an injector main body 5, a slider 6, an injection cylinder 7, a rotary member 8, a plunger 9, and a rod 10 (located and concealed inside the intraocular lens injector 1 in FIG. 3). Preferably, each of these constituent elements is constituted by resin molded products.

The injector main body 5 and the injection cylinder 7 each have a hollow structure and are coupled to each other to thereby constitute a hollow body. As described above, the present disclosure is remarkably characterized by a shape of the inner wall of the tube of the hollow body.

The slider 6 is attached to the injector main body 5. By advancing the slider 6, the intraocular lens 4 is advanced, and bent into a valley-fold shape (bent downward) along the narrowing inner diameter of the injection cylinder main body 7*a*. The bent intraocular lens 4 is advanced by the plunger 9 and thus the rod 10, and discharged from the nozzle portion 7*b*.

The injection cylinder 7 is arranged so as to communicate with a tip portion of the injector main body 5. The injection cylinder 7 and the tip portion of the injector main body 5 may be integrally molded, or may be separately molded and the injection cylinder 7 may be attached to the tip portion. The injection cylinder 7 has a hollow injection cylinder main body 7*a* and a narrow tubular nozzle portion 7*b*.

At this time, the lens installation portion 11 of the injector main body 5 is accommodated and arranged, together with the intraocular lens 4 installed therein, inside the injection cylinder main body 7*a* of the injection cylinder 7. An inlet 7*c* is formed on a top surface of the injection cylinder main body 7*a*. The inlet 7*c* is for injecting the viscoelastic substance (e.g., sodium hyaluronate). The viscoelastic substance injected through the inlet 7*c* is supplied to the intraocular lens 4 installed in the lens installation portion 11.

The rotary member 8 is rotatably connected to a rear end portion of the injector main body 5.

The plunger 9 is arranged coaxially with the injector main body 5. A part of the plunger 9 is arranged inside the injector main body 5 through the rotary member 8, and the other part of the plunger 9 is arranged to protrude rearward from the rotary member 8.

The rod 10 is arranged inside a hollow body consisting of the injector main body 5 and the injection cylinder 7. The rod 10 is connected to the plunger 9, and plays a role in advancing the intraocular lens 4.

As shown in FIG. 4, the lens installation portion 11 includes a bottom surface portion 11*a*, a lens receiving portion 11*b*, and a lens guide portion 11*c*. The lens receiving portion 11*b* receives and supports the intraocular lens 4 from below. The intraocular lens 4 is installed in the lens installation portion 11 in a state in which the front support portion 42*a* is arranged, as its name suggests, frontward (X1 direction), and the other rear support portion 42*b* is arranged, as its name suggests, rearward (X2 direction). The intraocular lens injector 1 is a preload type with the intraocular lens 4 is previously installed in the lens installation portion 11 of the injector main body 5. Therefore, the intraocular lens 4 is one of the constituent elements of the intraocular lens injector 1. However, in executing the present invention, the intraocular lens injector is not necessarily required to be the preload type.

Configuration of Case

As for the configuration of the case, for example, the configuration disclosed in Japanese Patent No. 5254669 by the present applicant may be adopted. Regarding the configuration of the case, for the contents not described below, the configuration described in Japanese Patent No. 5254669 can be applied, and the description of Japanese Patent No. 5254669 is incorporated herein as if fully set forth in the present specification.

If the description in the above-described WO 2018/003854 differs from the description in the specification of Japanese Patent No. 5254669, the description in the above-described WO 2018/003854 shall prevail. For example, the specification of Japanese Patent No. 5254669 states that the intraocular lens 4 is installed in the lens installation portion with the front support portion bent by a protruding portion 80, but in this embodiment, the position where the intraocular lens 4 is placed in its pre-bent state as described in WO 2018/003854 is regarded as the lens installation portion 11.

Figure 5:
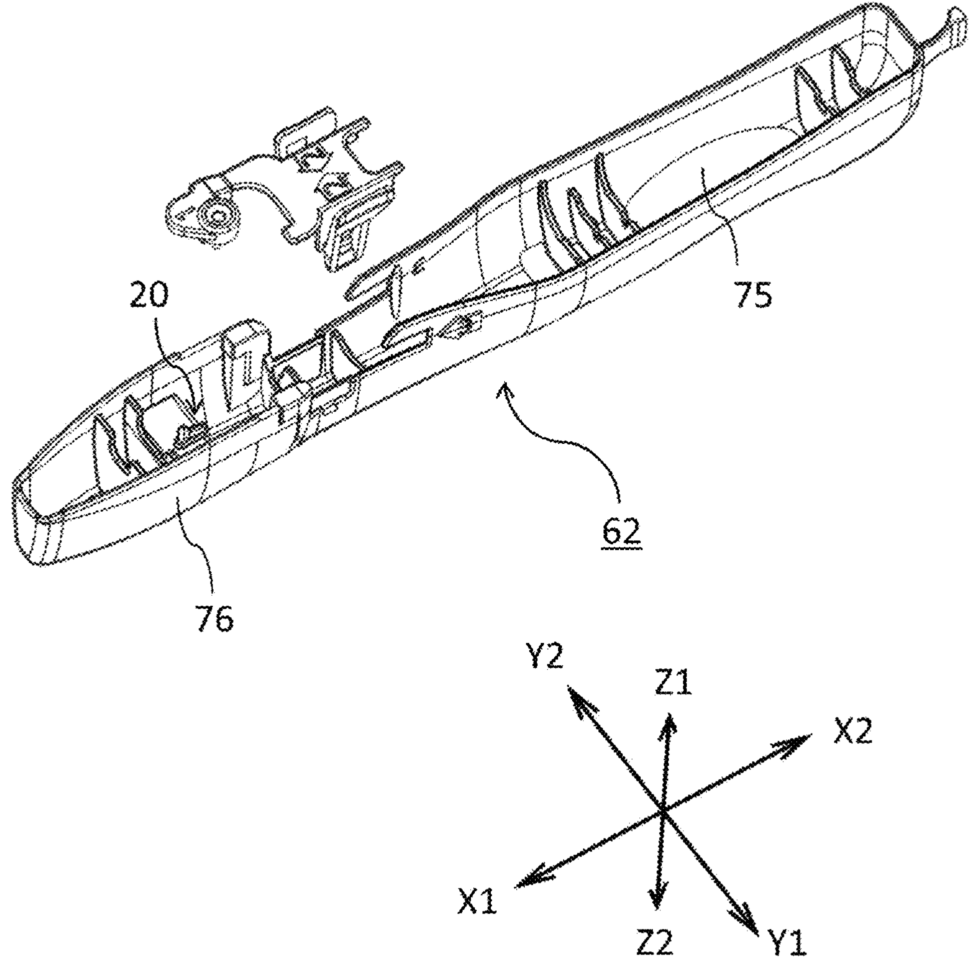
FIG. 5 is a perspective diagram illustrating an intraocular lens injector case.

FIG. 5 is a perspective diagram of the case of the intraocular lens injector according to an embodiment of the present disclosure.

Figure 6:
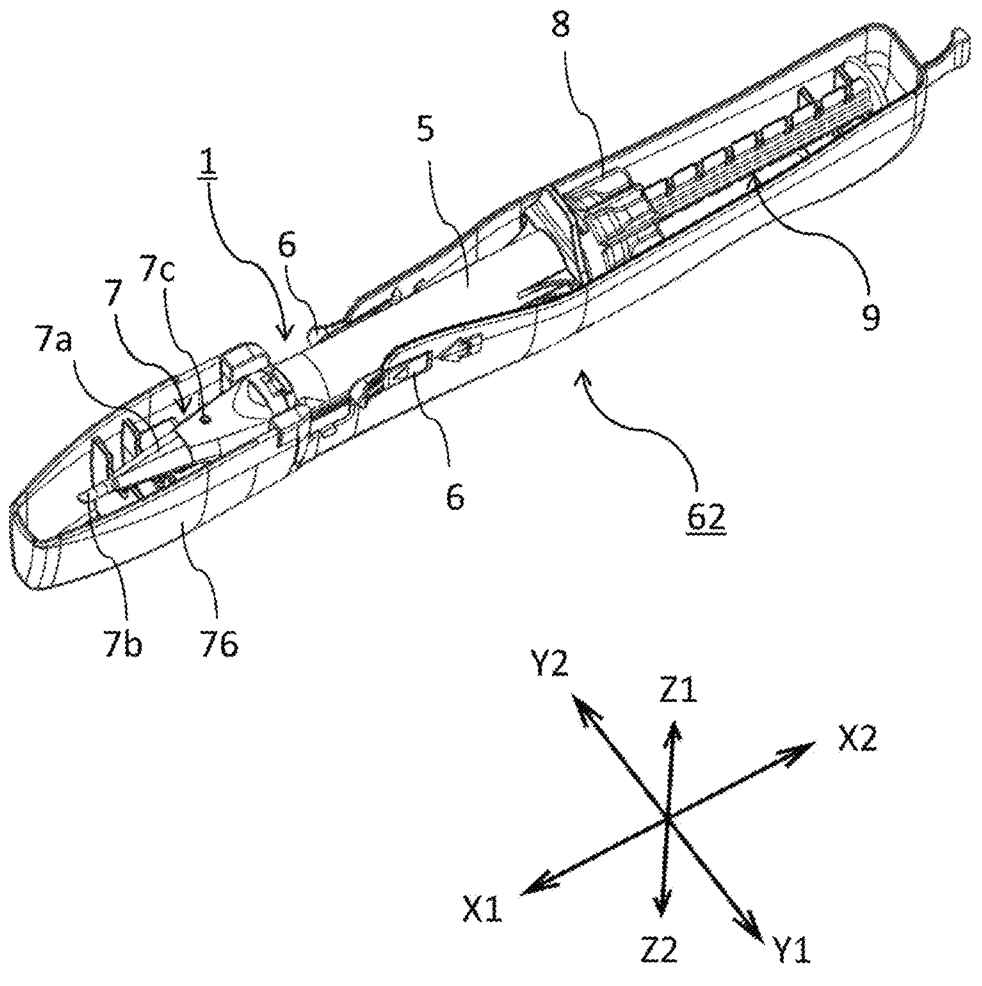
FIG. 6 is a perspective diagram illustrating how the intraocular lens injector is attached to the case.

FIG. 6 is a perspective diagram illustrating how the intraocular lens injector according to the embodiment of the present disclosure is attached to the case.

Figure 10:
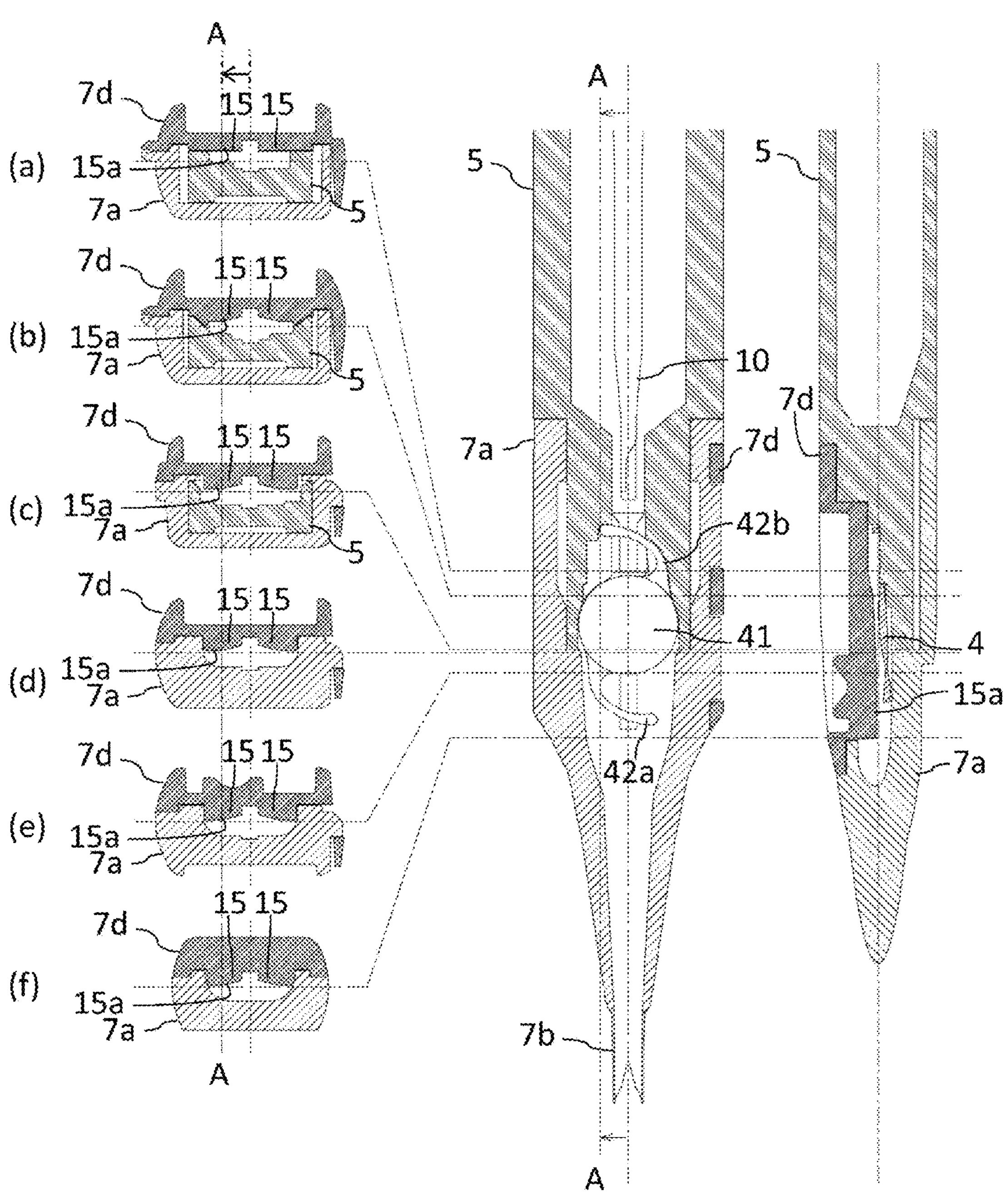
FIG. 10 is a cross-sectional diagram of another intraocular lens injector. The middle panel is an X-Y cross-sectional diagram passing through a midpoint of up and down axis of the intraocular lens injector, a right panel is an X-Z cross-sectional diagram passing through the A-A line in the middle panel, and left panels (a) to (f) are Y-Z cross-sectional diagrams.

The intraocular lens injector 1 according to this embodiment can be detachably attached to a case 62 which is integrally molded, for example, from a synthetic resin material. As shown in FIG. 10 of Japanese Patent No. 5254669 (corresponding to FIG. 5 of the present application), the case 62 has a U-shaped wall portion 76 standing on a bottom plate portion 75 so as to surround the intraocular lens injector 1, and a tucking pin 20 standing at a predetermined position on the bottom plate portion 75.

Figure 11:
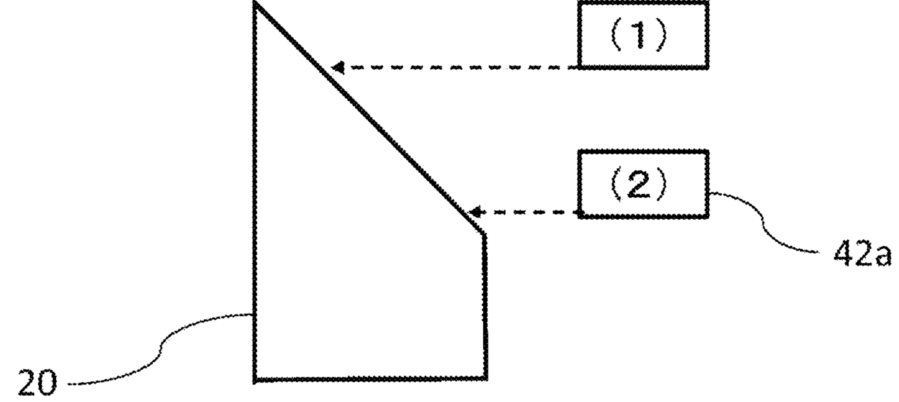
FIG. 11 is a schematic cross-sectional diagram of an X-Z plane illustrating a positional relation between the front support portion and the tucking pin when advancing the intraocular lens.
Figure 11:
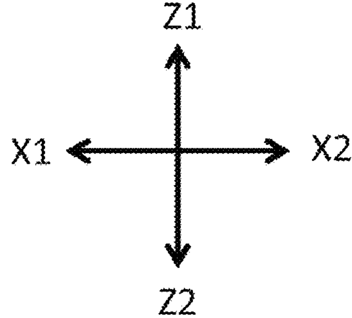

The tucking pin 20 is configured so as to be injected into a protrusion injection hole 73 of the intraocular lens injector 1 when the intraocular lens injector 1 is attached to the case 62, as shown in FIG. 11 of Japanese Patent No. 5254669 (corresponding to FIG. 6 of the present application). As a result, in the intraocular lens injector 1, the tucking pin 20 of the case 62 is arranged in the central region of the movable space of a tip member 71.

As shown in FIG. 6, with the intraocular lens injector 1 attached to the case 62, the intraocular lens 4 placed in the lens installation portion 11 is advanced toward a discharge hole of the nozzle portion 7*b* by the slider 6. When a configuration without the slider 6 is adopted, this advancement may be made by the plunger 9 (directly by the rod 10 linked to the plunger 9). Therefore, the rod 10 linked to the slider 6 or the plunger 9 is also called an advancing member.

Due to this advancement, the intraocular lens 4 is bent into an approximate U-shape with the front support portion 42*a* abutting the tucking pin 20 and a tip of the front support portion 42*a* being folded backward (X2 direction), in the opposite direction of a lens advancement direction (forward, X1 direction).

The intraocular lens injector 1 can be detached from the case 62 while remaining in this state, and the intraocular lens 4 can be pushed forward (in X1 direction) by the plunger 9 with the front support portion 42*a* being bent, and the intraocular lens 4 can be injected into the eye through the nozzle portion 7*b*.

The main feature of this embodiment is the protrusion located on both left and right corners on the inner wall in the tube through which the intraocular lens passes toward the nozzle. Other than the above feature, the configuration of the known intraocular lens injector may be adopted. For example, the configuration of WO 2018/003854 by the present applicant may be adopted. For the contents not described below, the configuration of the known intraocular lens injector (for example, the configuration of WO 2018/003854) shall be adopted, and the description of WO 2018/003854 is incorporated herein as if fully set forth in the present specification.

Figure 1:
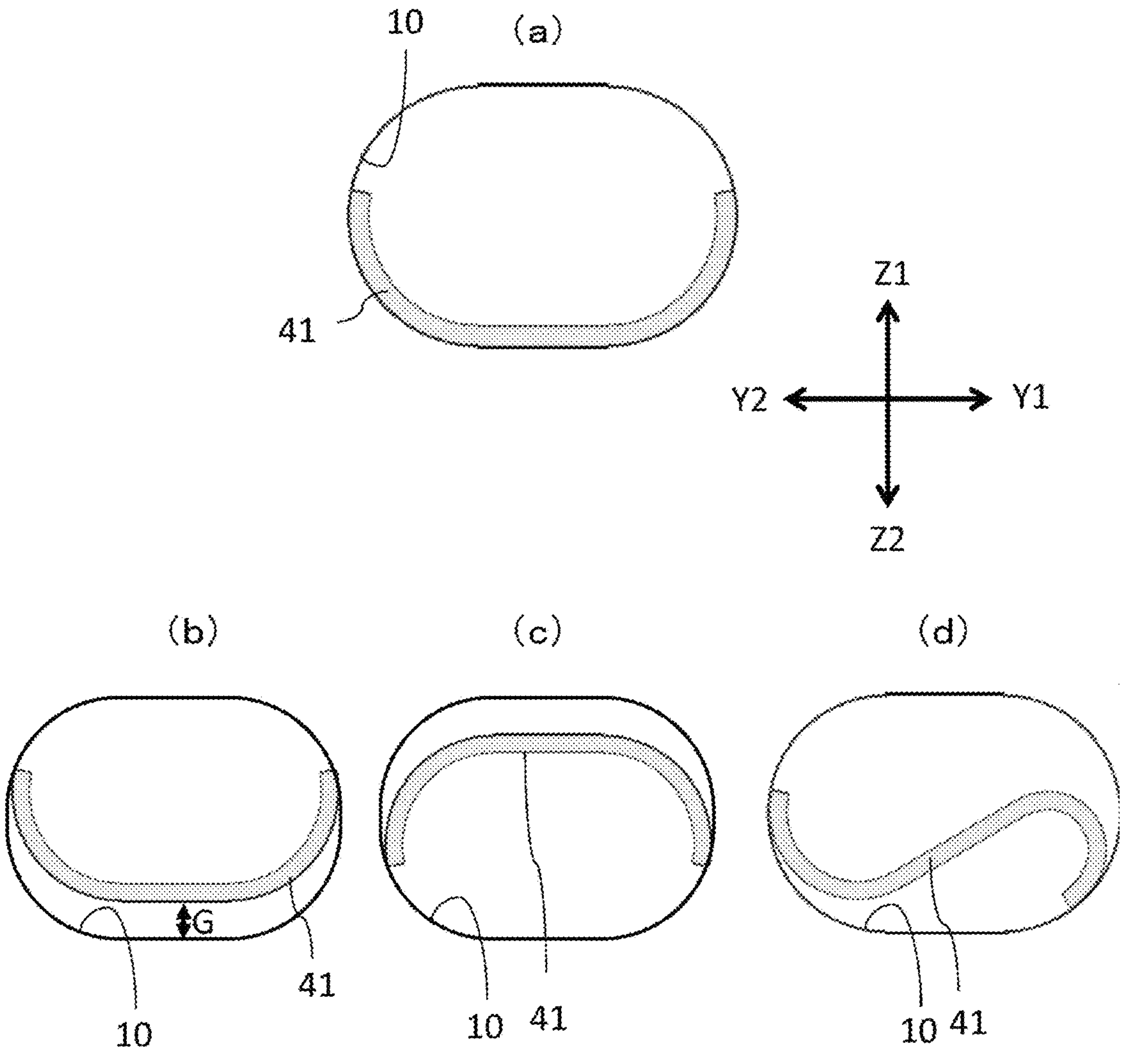
FIG. 1 is a schematic cross-sectional diagram illustrating an inner wall of a tube leading to a nozzle of an intraocular lens injector.

In addition, FIG. 3 and FIG. 4 of the present application are similar in configuration to FIG. 1 and FIG. 6 of WO 2018/003854, except for the intraocular lens 4. Therefore, the reference numerals in FIG. 4 of the present application that are not described herein are as described in WO 2018/003854.

Feature of Intraocular Lens Injector According to this Embodiment

The following sections focus on the features of the intraocular lens injector according to this embodiment.

The configuration of the feature of the intraocular lens injector according to this embodiment is as follows:

"an intraocular lens injector that advances an intraocular lens including an optical portion with an optical function and support portions that extend from the optical portion through a tube while folding the lens, and injects the lens from a nozzle, wherein protrusions are located at both left and right corners at an upper side of an inner wall of the tube, in a cross-sectional view perpendicular to an advancement direction of the intraocular lens, so that the protrusions prevent the optical portion and the support portions from entering both the left and right corners, when the intraocular lens is folded while advancing."

This embodiment is remarkably characterized by a shape of the inner wall of the tube in the intraocular lens injector. The tube is formed by the injector main body and the injection cylinder that constitute the hollow structure. The term "inner wall" used herein is a portion of the intraocular lens, forming an innermost contour of the tube that is a passage through which the intraocular lens passes in a cross-sectional view perpendicular to the advancement direction (the cross-sectional view on the Y-Z plane).

In Patent Documents 1 and 2, both the left and right corners at the upper side of the inner wall of the tube retain their concave shape, although protrusions are formed downward from the top plate portion. Specifically, in FIG. 4 of Patent Document 1, the inner wall at the left corner indicated by the reference numeral 42 on the left side and the inner wall at the right corner indicated by the reference numeral 44 on the right side retains a concave shape (convex toward the outside of the tube). The same applies to the inner wall at the left corner indicated by the reference numeral 46 on the left side and the inner wall at the right corner indicated by the reference numeral 44 on the right side in FIG. 5 of Patent Document 2.

On the other hand, in this embodiment, the protrusions are located at both left and right corners at an upper side of the inner wall of the tube in a cross-sectional view perpendicular to the advancement direction of the intraocular lens (in a cross-sectional view on the Y-Z plane). Hereinafter, the description of the inner wall of the tube is based on the cross-sectional view (the cross-sectional view on the Y-Z plane) unless otherwise specified. As described in the section of Problems to be Solved by Disclosure, this configuration is based on the new finding that the incursion of the optical portion or the support portion into both the left and right corners affects the folding accuracy.

In this embodiment, there is no limitation on the shape of the inner wall of the tube in the cross-sectional view. The shape in the cross-sectional view before the protrusions of this embodiment are formed is an elliptical shape with a major axis in Y1-Y2 and a minor axis in Z1-Z2, as shown in FIG. 2.

Figure 7:
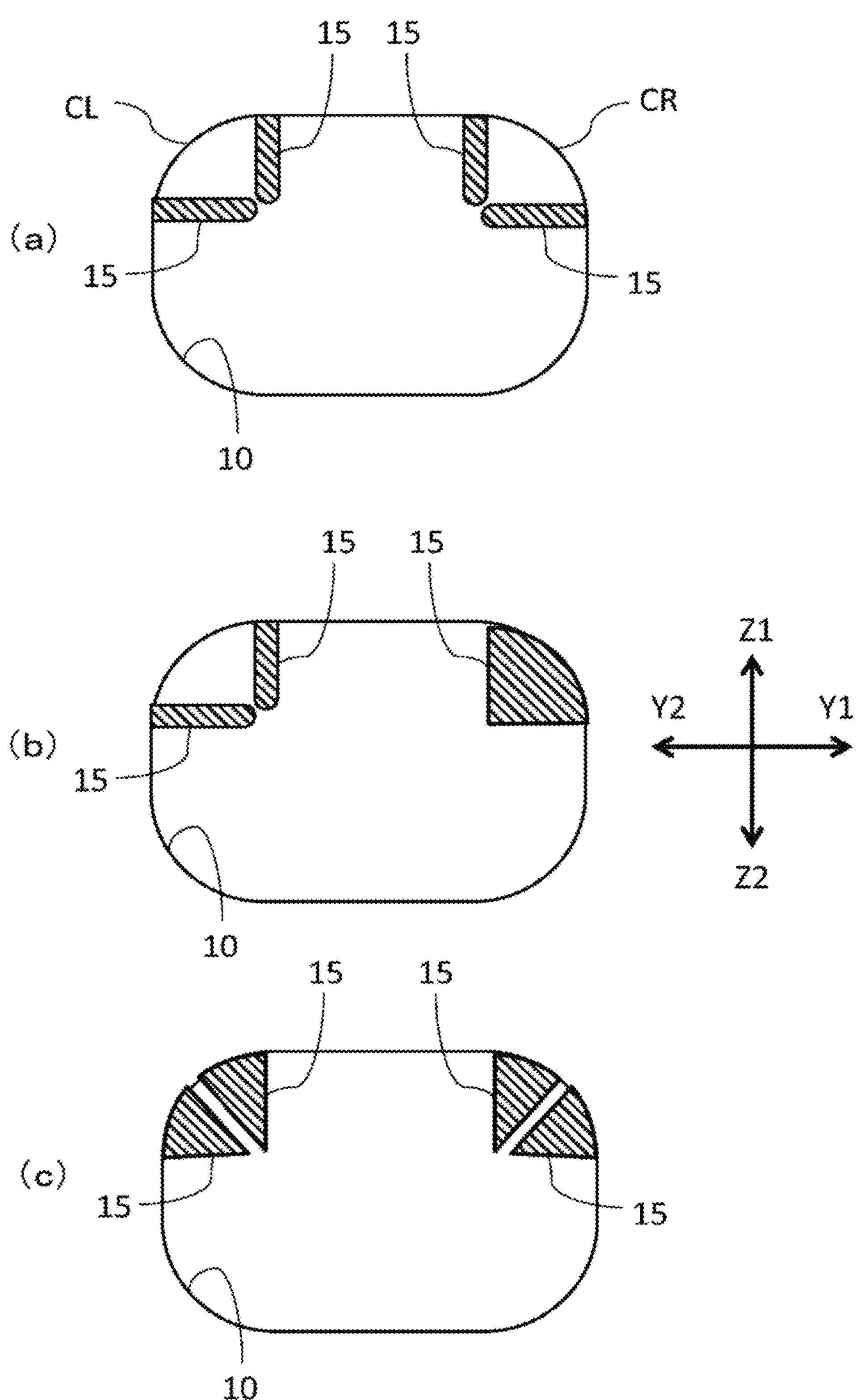
FIG. 7 is a schematic cross-sectional diagram illustrating a modified example of the protrusion.

FIG. 7 is a schematic cross-sectional diagram illustrating a modified example of the protrusion.

Figure 2:
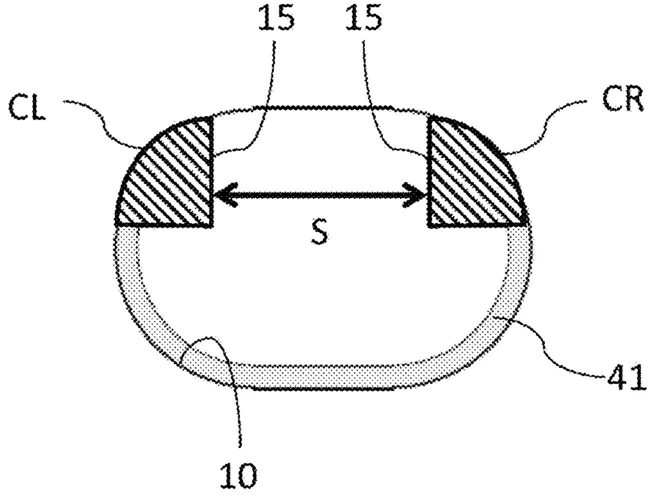
FIG. 2 is a schematic cross-sectional diagram illustrating how protrusions are located at both left and right corners of the inner wall of the tube leading to the nozzle of the intraocular lens injector.
Figure 2:
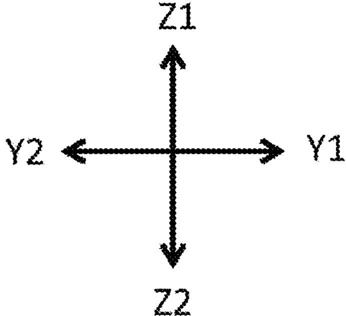

Both the left and right corners in this embodiment refer to the vicinity of both the left and right corners (vicinity of CR, CL in FIG. 2) in a virtual cross-sectional contour formed by continuously changing the curvature between both ends of the protrusion in FIG. 2. In a case where both the left and right corners are not covered but separated by the protrusions as shown in FIG. 7(*a*), both the left and right corners refer to the vicinity of both the left and right corners (vicinity of CR, CL in FIG. 2) in an actual cross-sectional contour.

In the cross-sectional view, the protrusion is a portion where the curvature changes sharply at a base portion of the protrusion. For example, a state where the curvature of the base portion of the protrusion is 10 times or more greater than the curvature of the vicinity of the base portion of the protrusion (i.e., the shape of the inner diameter of the tube in the vicinity of the protrusion) may be considered as the protrusion. Alternatively, a position where the curvature changes discontinuously from the curvature of the vicinity of the base of the protrusion may be considered as the base of the protrusion.

Due to the shape of the inner wall of the tube of this embodiment, the area wherein the optical portion and the support portion can move can be reduced. As a result, the optical portion can be folded into the valley-fold shape with its posture corrected to the state shown in FIG. 1(*a*), and both of the front support portion and the rear support portion can be tucked into the optical portion, and thus the intraocular lens can be folded with high accuracy.

There is no limitation on the aspects (number, material, shape, etc.) of the protrusion, so long as neither the optical portion nor the support portions enter both the left and right corners, while the folded intraocular lens is advancing.

As for the number of the protrusions, there may be one for each of both the left and right corners (two in total) as shown in FIG. 2, or there may be one for each of both the left and right corners, with one protruding downward and the other protruding inward horizontally (FIG. 7(*a*)). Both the left and right corners may have a different number of protrusions (FIG. 7(*b*)). For example, it is not precluded to provide more than one protrusion properly spaced so as to not to tuck the optical portion nor the support portion there between (FIG. 7(*c*)).

As for the material of the protrusion, the material of the protrusion is the same as those used for the injector main body and the hollow body which is an injection cylinder formed by injection molding, which is preferable. However, different material may be acceptable.

As for the shape of the protrusion, it is preferable that a space (e.g., reference sign S in FIG. 2) is formed between both the left and right corners, having a width in which the folded support portions can be accommodated, due to the protrusions.

In a case of adopting the intraocular lens described in the section basic configuration of intraocular lens injector according to this embodiment, the front support portion and the rear support portion extend from the optical portion, in the intraocular lens. Depending on the intraocular lens injector, the rear support portion is bent so as to be placed over the optical portion, and then the intraocular lens is advanced. In the present specification, bending the support portion so as to be placed over the optical portion is referred to as "tucking".

In a case where the rear support portion is tucked in advance, when a space S is formed between both the left and right corners, having a width in which the folded support portions can be accommodated, the rear support portion is accommodated in the space S upon advancement of the intraocular lens. Without the space S, the tucked rear support portion comes into contact with the left and right protrusions. When the intraocular lens advances while maintaining the contact, the tucking may be released due to friction caused by the left and right protrusions. This space S can reduce the possibility of the event occurring.

As described in WO 2018/003854, when the slider is used to move the intraocular lens to the initial stage of extrusion before being advanced by the rod, the tip portion of the slider may be accommodated in the space S described in the above paragraph.

Unlike Patent Documents 1 and 2, the protrusions preferably protrude inward horizontally and also protrude downward at both the left and right corners, as shown in FIG. 2. This configuration ensures that neither the optical portion nor the support portion can enter both the left and right corners.

The protrusion described in the previous paragraph is a protrusion of the stepped shape as shown in FIG. 2, and it is preferred in that it ensures neither the optical portion nor the support portion can enter both the left and right corners. The protrusion of the stepped shape may have rounded steps so long as the posture of the optical portion is corrected.

The positional relation of the protrusions will be specified below.

Figure 8A:
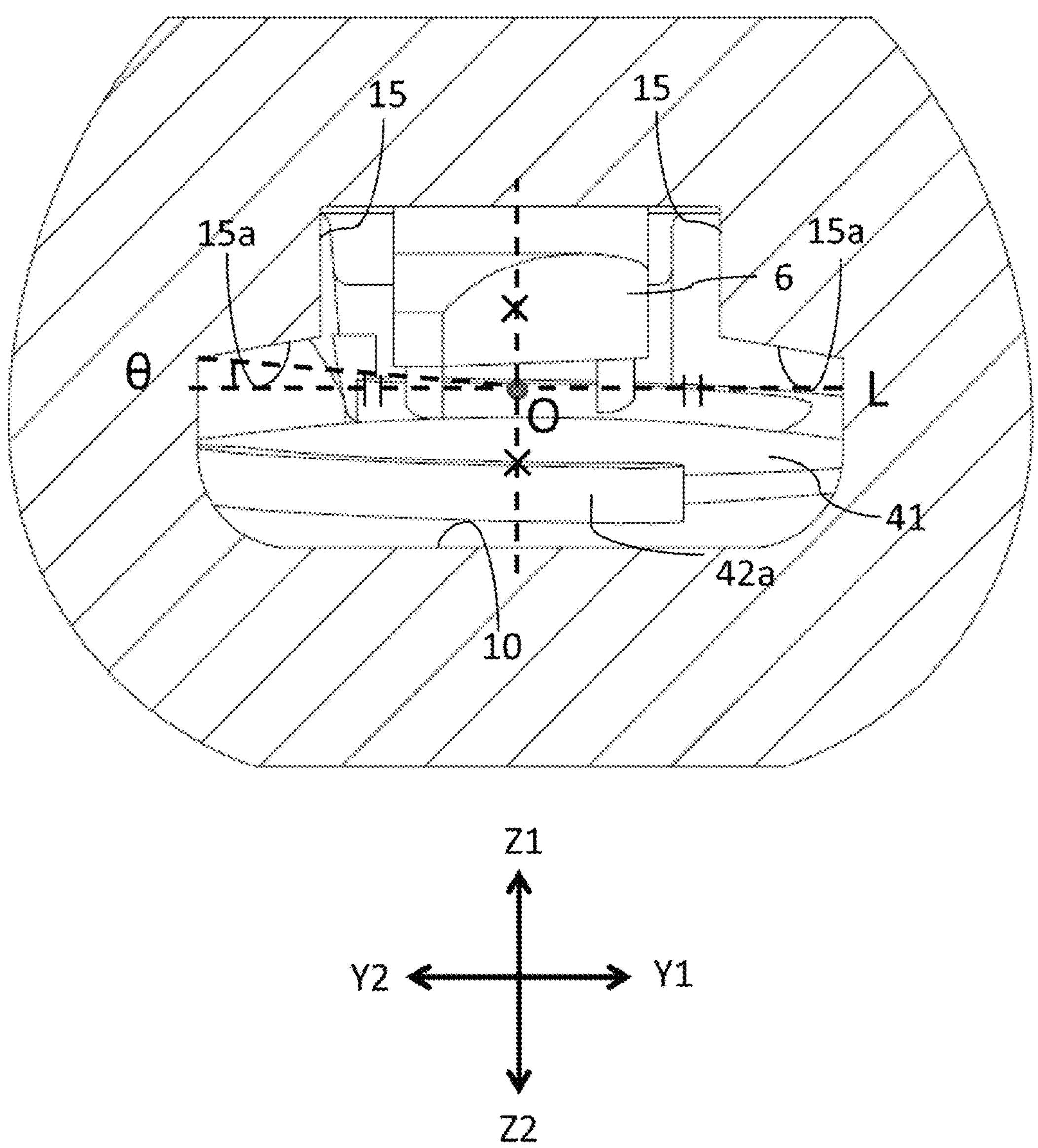
FIG. 8A is a schematic cross-sectional diagram (Part 1) specifying the positional relationship of the protrusions.
Figure 8B:
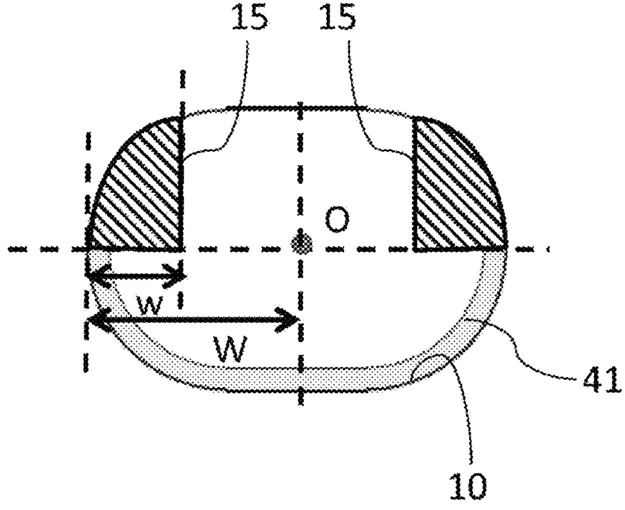
FIG. 8B is a schematic cross-sectional diagram (Part 2) specifying the positional relationship of the protrusions.
Figure 8B:
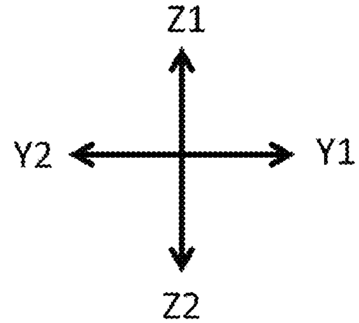
Figure 8C:
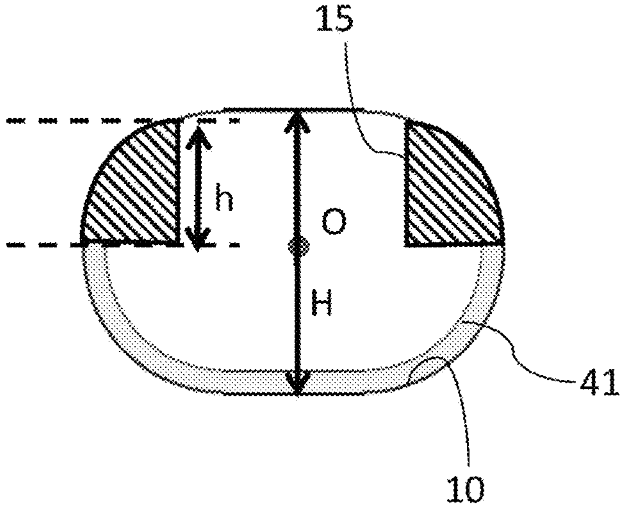
FIG. 8C is a schematic cross-sectional diagram (Part 3) specifying the positional relationship of the protrusions.
Figure 8C:
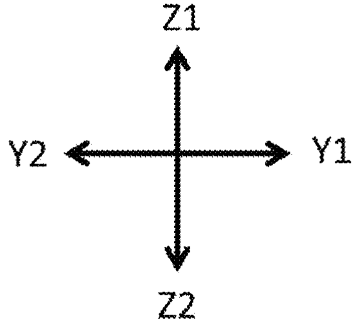

FIG. 8A to FIG. 8C are schematic cross-sectional diagrams (Part 1 to Part 3) for explaining a method of specifying the positional relation of the protrusions.

The cross-sectional shape of the inner wall of the tube without protrusions is provided. Then, a horizontal line L passing through a point O, a midpoint of up, down, left and right of the shape, is assumed. In the present specification, the direction from the inner wall toward the point O is referred to as inside, and the opposite side is referred to as outside.

Then, the protrusion preferably exists on the inner wall with the inclination angle θ within any of a range of 0 to 20 degrees (preferably 0 to 15 degrees, more preferably 10 to 15 degrees) from this horizontal line. In this embodiment, the inner wall within entire or any of a range of 0 to 20 degrees of the inclination angle θ may be set as both the left and right corners at the upper side. However, the present invention does not preclude the protrusion existing on the inner wall within a range of less than 0 degrees or more than 20 degrees of θ.

A minimum value of the inclination angle θ in the part where the protrusions exist is preferably in a range of 0 to 15 degrees. In other words, it is preferable that the starting position of the protrusion has the inclination angle θ within a range from 0 to 15 degrees, and the protrusion is located continuously or discontinuously against the inner wall from the starting position as θ increases.

It is preferable that the protrusions have a shape that changes a concave shape (protruding outward) of both the left and right corners to a convex shape (protruding inward) in the cross-sectional shape of the inner wall. Alternatively, the protrusion may be located at a position where the cross-sectional shape of the inner wall has the largest rate of change in curvature.

For example, a width w in the Y1-Y2 direction of the protrusion (e.g., protrusion with stepped shape) located at the left corner is preferably 10 to 60% of a width W from a predetermined position on the vertical line formed of mid-points of left and right (e.g., a midpoint O of up, down, left and right) to the left inner wall. As for an actual size, the width in the Y1-Y2 direction of the protrusion located at the left corner is set to 0.5 to 2.5 mm. The same preferred examples may also be applied to the protrusion located at the right corner.

For example, as in FIG. 8C, a height h in the Z1-Z2 direction of the protrusion (e.g., protrusion with stepped shape) located at the left corner is preferably 30 to 80% of a height H between an upper-side inner wall and a lower-side inner wall on a vertical line passing through the above-described midpoint O of up, down, left and right. As for an actual size, the height in the Z1-Z2 direction of the protrusion located at the left corner is set to 0.5 to 1.5 mm. The same preferred examples may also be applied to the protrusion located at the right corner.

Figure 9:
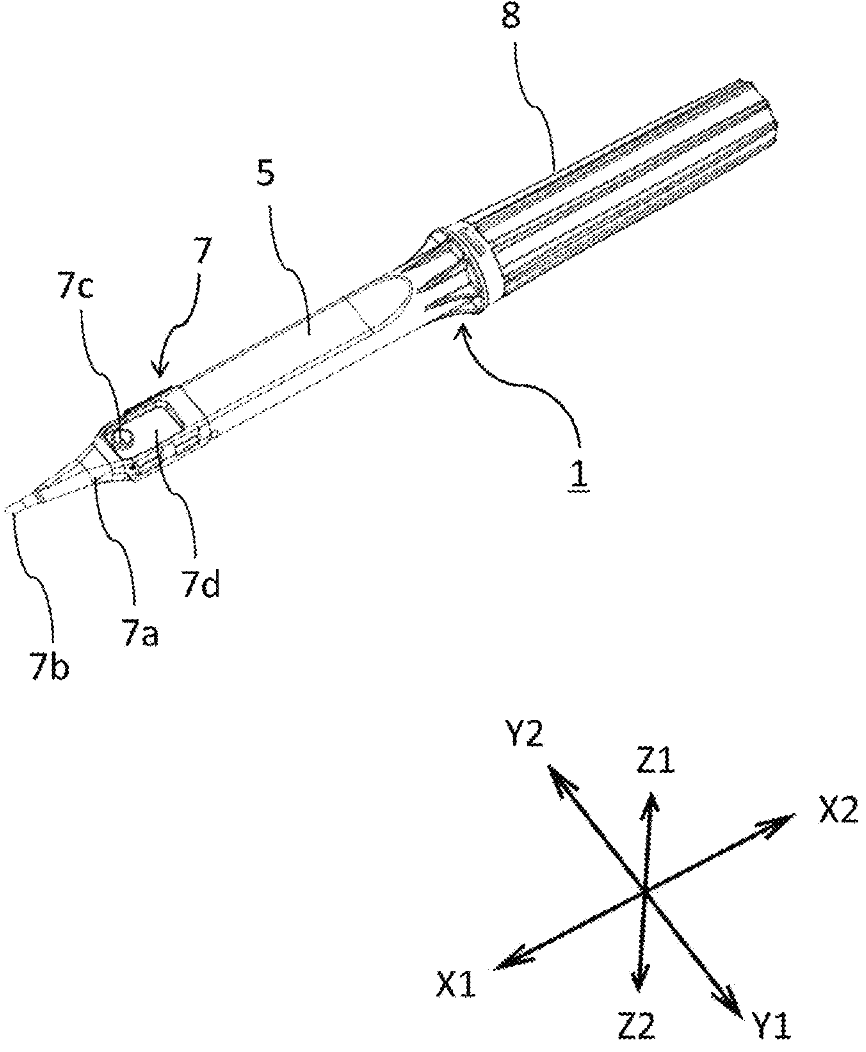
FIG. 9 is a perspective diagram of another intraocular lens injector.

FIG. 9 is a perspective diagram of another intraocular lens injector.

FIG. 10 is a cross-sectional diagram of another intraocular lens injector. A middle panel is an X-Y cross-sectional diagram passing through a midpoint of up and down of the intraocular lens injector, a right panel is an X-Z cross-sectional diagram passing through the A-A line in the middle panel, and left panels (a) to (f) are Y-Z cross-sectional diagrams.

FIG. 3 to FIG. 6 so far described show the intraocular lens injector 1 using the slider 6, while FIG. 9 and FIG. 10 show the intraocular lens injector 1 without the slider 6. Also, a lid *7d* is located above the lens installation portion 11. The lid *7d* can be opened and closed. FIG. 10 illustrates an example where protrusions 15 are located on a lid *7d*, so that when the lid *7d* is closed, the protrusions 15 may be consequently formed at both the left and right corners in the tube.

The arrangement of the protrusion (e.g., protrusion with stepped shape) in the X1-X2 (front-back) direction is not limited as long as it allows for the tucking of the front support portion for the optical portion to be completed normally when advancing the intraocular lens. From the viewpoint of folding the intraocular lens 4 with high accuracy, it is preferable to locate the protrusion at a position that contributes to folding.

It is preferable to locate the protrusion at the position where the optical portion 41 exists after the start of the folding of the intraocular lens 4. In FIG. 10, it is preferable to locate the protrusion at least between (e) and (f). Putting "between (e) to (f)" in another way, when the intraocular lens 4 is installed in the lens installation portion 11, it is preferable to have a protrusion at least between the front end of the optical portion 41 and the front end of the front support portion *42a*, the protrusion being preferably formed lengthwise in a front-back direction and to include both the front ends.

However, as shown in FIG. 10, the protrusion may be formed lengthwise between the position (FIG. 10(*a*)) where the optical portion 41 does not exist at the start of the folding of the intraocular lens 4 and the front end of the front support portion *42a*.

There is no limitation on the member on which the protrusion is located. However, as shown in FIG. 10, protrusions may be located on a lid *7d*, so that when the lid *7d* is closed, protrusions may be consequently located at both the left and right corners in the tube. Of course, when a preloaded type intraocular lens injector with no lid *7d* is employed, the protrusion may be located on both the left and right corners on the inner wall of the tube in the injection cylinder main body *7a*.

As shown in the right panel of FIG. 10, a lower end of the protrusion may be displaced downward as it moves forward. In particular, when the intraocular lens 4 is installed in the lens installation portion 11, it is preferable to displace the lower end of the protrusion downward as it moves forward, at least at the connection (e.g., a part extending from FIG. 10(*a*) to FIG. 10(*b*)) with a rear support portion *42b* for the optical portion 41, which helps proper tucking of the rear support portion *42b*.

The length of the protrusion in the X1-X2 direction is not limited as long as it is long enough to allow the tucking of the front support portion for the optical portion to be completed normally when advancing the intraocular lens. As for an actual size, the length in the X1-X2 direction of the protrusion located at the left corner is set to 5 to 15 mm. The same preferred examples may also be applied to the protrusion located at the right corner.

Next, a further effect of the intraocular lens injector according to this embodiment will be described.

In a case of adopting the slider, the protruding portion 20 is configured so as to be injected into a protrusion injection hole 73 of the intraocular lens injector 1 when the intraocular lens injector 1 is attached to the case 62, as shown in FIG. 5 and FIG. 6. As a result, in the intraocular lens injector 1, the protruding portion 20 of the case 62 is arranged in the central region of the movable space of a tip member 71.

With the intraocular lens injector 1 attached to the case 62, the intraocular lens 4 placed in the lens installation portion 11 is advanced toward a discharge hole of the nozzle portion *7b* by the slider 6.

Due to this advancement, the intraocular lens 4 is bent into an approximate U-shape with the front support portion *42a* abutting the protruding portion 20 and a tip of the front support portion *42a* being folded backward (X2 direction), in the opposite direction of a lens advancement direction (forward, X1 direction). The protruding portion 20 is also referred to as the tucking pin 20.

FIG. 11 is a schematic cross-sectional diagram of an X-Z plane illustrating a positional relation between the front support portion and the tucking pin when advancing the intraocular lens.

As shown in FIG. 11, the tucking pin 20 according to this embodiment preferably stands up upward and the surface that is in contact with the front support portion *42a* is a slope that slants upward towards the d front.

This configuration would facilitate the upward displacement of the front support portion after it contacts the tucking pin 20. In other words, with the tucking pin having a rectangular shape as indicated by the reference numeral 80 in FIG. 10 of Japanese Patent No. 5254669 in place of this configuration, it tends to be uncertain whether the front support portion will be displaced upward or downward after coming into contact with the tucking pin. An example in which the tucking pin has the above slope will be given below.

In the intraocular lens injector 1 according to this embodiment, the protrusions are located at both the left and right corners of the inner wall at the upper side as described above. Therefore, neither the optical portion 41 nor the support portions 42*a*, 42*b* can enter both the left and right corners when the intraocular lens 4 is folded as it advances. This means that the optical portion 41 and the support portions 42*a*, 42*b* are naturally arranged nearer to the lower side.

Since the optical portion 41 and the support portions 42*a*, 42*b* are arranged nearer to the lower side, the tucking pin 20 comes in contact with the front support portion 42*a* ((2) in FIG. 11 which is this embodiment) at the timing earlier than that in the conventional front support portion shown by (1) in FIG. 11. This reduces the risk of the front support portion 42*a* entering between the outer surface, which is opposite to the inner surface, of the optical portion 41, and the inner wall of the intraocular lens injector 1 during advancement of the intraocular lens.

In particular, when the intraocular lens 4 as a whole is formed of soft material, the support portions 42*a*, 42*b* of the intraocular lens 4 tend to be lifted up from the viscoelastic material due to the difference in specific gravity from the viscoelastic material that passes through the tube together with the intraocular lens 4. Even in such a case, by adopting the configuration according to this embodiment, both the optical portion 41 and the support portions 42*a*, 42*b* are naturally arranged nearer to the lower side.

Details of how the above-described effects were obtained will be described below.

The present inventor paid attention to the movement when the front support portion abuts against the protrusion portion described in the specification of Japanese Patent No. 5254669. As a result, with the protruding portion described in the specification of Japanese Patent No. 5254669, it is found that when the intraocular lens as a whole moves forward, the front support portion continues to bend backward and the timing of the tip of the front support portion moving to the vicinity of the inner wall of the intraocular lens injector tends to be very close to or earlier than the timing of the advancement of the periphery of the optical portion in the folded intraocular lens.

Therefore, in order to intentionally shift the timing, the present inventor created the technical idea that when the intraocular lens 4 as a whole advances, the tip of the front support portion 42*a*, which is bending backward, is displaced more quickly than before so as to hasten the timing of the movement of the front support portion 42*a* to the vicinity of the inner wall. In a case where the timing is earlier, the optical portion 41 does not yet exist nearby when the front support portion 42*a* moves to the vicinity of the inner wall. By the time the optical portion 41 approaches, the bending of the front support portion 42*a* has progressed and the front support portion 42*a* has already moved away from the vicinity of the inner wall. As a result, the possibility of the front support portion 42*a* being tucked between the optical portion 41 and the lower-side inner wall can be reduced.

In the above example, the intraocular lens injector adopting the slider is exemplified, but the present invention can also be applied even when the intraocular lens is advanced only by the rod 10 (plunger 9) without using the slider. In other words, the present disclosure can be applied with or without the slider and is highly versatile.

Design Method of Intraocular Lens Injector According to this Embodiment

The present disclosure has technical significance as the design method of the intraocular lens injector as well. The contents are as follows:

"A design method of an intraocular lens injector that advances an intraocular lens including an optical portion with an optical function and a support portion that extends from the optical portion through a tube while folding the lens, and emits the lens from a nozzle, the method including:

providing protrusions at both left and right corners at an upper side of an inner wall of the tube, in a cross-sectional view perpendicular to an advancement direction of the intraocular lens, so that the protrusions prevent the optical portion and the support portions from entering both the left and right corners, when the intraocular lens is folded while advancing."

The feature of the design method of the intraocular lens injector according to this embodiment resides in that the shape of the inner wall of the tube through which the intraocular lens passes is changed from the basic design before the design change.

In general, changing the shape of the inner wall of the tube of the intraocular lens injector remarkably changes the folding behavior of the intraocular lens. Even when the basic design before the design change had achieved some satisfactory results, there is a possibility that the design change attempted to improve the folding accuracy of the intraocular lens may result in the unexpectedly changed folding behavior of the intraocular lens.

On the other hand, the design method of the intraocular lens injector according to this embodiment would not need to change the cross-sectional shape of the inner wall of the tube except to provide the protrusion to both the left and right corners at the upper side of the inner wall of the tube as shown in FIG. 2, for example, with respect to the basic design of the inner wall of the tube before design change (e.g. FIG. 1(*a*)).

Note that the intraocular lens injector in which only difference between the shape of the inner wall of the tube before the design change and the shape of the inner wall of the tube after the design change is the protrusion described above can be considered to employ the design method of the intraocular lens injector according to this embodiment.

The technical scope of the present disclosure is not limited to the embodiments described above but includes various modes and modifications as far as the specific effects obtained by the constituent features of the disclosure and combinations thereof can be derived.

LIST OF REFERENCE NUMERALS AND SIGNS

1 . . . Intraocular lens injector
5 . . . Injector main body
6 . . . Slider
7 . . . Injection cylinder
7*a* . . . Injection cylinder main body
7*b* . . . Nozzle portion
7*c* . . . Inlet
7*d* . . . Lid

8 . . . Rotary member
9 . . . Plunger
10 . . . Rod
11 . . . Lens installation portion
11*a* . . . Bottom surface portion
11*b* . . . Lens receiving portion
11*c* . . . Lens guide portion
15 . . . Protrusion
15*a* . . . Lower end (of protrusion)
30 . . . Inner wall of tube
73 . . . Protrusion injection hole
62 . . . Case
20 . . . Protruding portion (tucking pin)
75 . . . Bottom plate portion
76 . . . O-shaped wall portion
4 . . . Intraocular lens
41 . . . Optical portion
41*a* . . . Effective optical portion
41*b* . . . Peripheral portion
42*a* . . . Front support portion
42*b* . . . Rear support portion

The invention claimed is:

1. An intraocular lens injector, comprising:

an intraocular lens including an optical portion and support portions;

a tube, through which the intraocular lens advances in an advancement direction, including a lens installation portion that holds the intraocular lens in such a manner that one support portion defines a front support portion and one support portion defines a rear support portion, an inner wall having an upper side with left and right corners, a lower side, and a location where the optical portion is located when the intraocular lens begins to valley fold towards the lower side as it advances in the advancement direction, a nozzle through which the intraocular lens is emitted, and protrusions that are located at both left and right corners at the upper side of the inner wall of the tube, in a cross-sectional view perpendicular to the advancement direction of the intraocular lens, a portion of each protrusion being located at a location between a front end of the optical portion and a front end of the front support portion of the intraocular lens when the intraocular lens is installed in the lens installation portion prior to moving in the lens advancement direction and where the optical portion will be located when the intraocular lens begins to valley fold while moving in the lens advancement direction such that the protrusions prevent the optical portion and the support portions from entering both the left and right corners of the upper side of the inner wall of the tube when the intraocular lens is valley folded while advancing.

2. The intraocular lens injector according to claim 1, wherein due to the protrusions, a space is formed between both the left and right corners, having a width in which the folded support portions can be accommodated.

3. The intraocular lens injector according to claim 2, wherein the protrusions protrude inward horizontally and also protrude downward.

4. The intraocular lens injector according to claim 2, wherein the protrusions exist on the inner wall within any of a range of 0 to 20 degrees of an inclination angle from a horizontal line passing through a midpoint of up, down, left and right of a cross-sectional shape of the inner wall of the tube.

5. The intraocular lens injector according to claim 4, wherein the protrusions have a shape that changes a concave shape of both left and right corners to a convex shape in the cross-sectional shape of the inner wall.

6. The intraocular lens injector according to claim 1, wherein the protrusions protrude inward horizontally and also protrude downward.

7. The intraocular lens injector according to claim 6, wherein the protrusions exist on the inner wall within any of a range of 0 to 20 degrees of an inclination angle from a horizontal line passing through a midpoint of up, down, left and right of a cross-sectional shape of the inner wall of the tube.

8. The intraocular lens injector according to claim 7, wherein the protrusions have a shape that changes a concave shape of both left and right corners to a convex shape in the cross-sectional shape of the inner wall.

9. The intraocular lens injector according to claim 1, wherein the protrusions exist on the inner wall within any of a range of 0 to 20 degrees of an inclination angle from a horizontal line passing through a midpoint of up, down, left and right of a cross-sectional shape of the inner wall of the tube.

10. The intraocular lens injector according to claim 9, wherein a minimum value of the inclination angle in the part where the protrusions exist is in a range of 0 to 15 degrees.

11. The intraocular lens injector according to claim 9, wherein the inner wall has a shape that changes from a concave shape of both left and right corners to a convex shape in the cross-sectional shape at the protrusions.

12. The intraocular lens injector according to claim 1, further comprising:

a tucking pin that bends a front support portion in contact with the front support portion, the front support portion being one of the support portions and arranged in front, wherein the tucking pin stands upward and a surface of the tucking pin that comes into contact with the front support portion is a slope that slants upwards toward the front.

13. A method of an intraocular lens injector that advances an intraocular lens, the intraocular lens including an optical portion with an optical function and defining a front end and a front support portion that extends from the optical portion and defines a front end, from a lens installing portion through a tube while folding the lens beginning at a location between the front end of the optical portion and the front end of the front support portion, and emits the lens from a nozzle, the method comprising:

providing protrusions at both left and right corners at an upper side of an inner wall of the tube, in a cross-sectional view perpendicular to an advancement direction of the intraocular lens, with a portion of each protrusion at a location between the front end of the optical portion and the front end of the front support portion of the intraocular lens when the intraocular lens is installed in the lens installation portion prior to moving in the lens advancement direction and where the optical portion will be located when the intraocular lens begins to valley fold while moving in the lens advancement direction so that the protrusions prevent the optical portion and the support portions from entering both of the left and right corners when the intraocular lens is valley folded while advancing.

* * * * *